United States Patent
Antzelevitch et al.

(10) Patent No.: US 7,745,213 B2
(45) Date of Patent: Jun. 29, 2010

(54) MUTATIONS IN ION CHANNEL PROTEINS ASSOCIATED WITH SUDDEN CARDIAC DEATH

(75) Inventors: Charles Antzelevitch, New Hartford, NY (US); Ramon Brugada, New Hartford, NY (US); Kui Hong, Utica, NY (US)

(73) Assignee: Masonic Medical Research Laboratory, Utica, NY (US)

( * ) Notice: Subject to any disclaimer, the term of this patent is extended or adjusted under 35 U.S.C. 154(b) by 0 days.

(21) Appl. No.: 12/413,735

(22) Filed: Mar. 30, 2009

(65) Prior Publication Data

US 2009/0317905 A1 Dec. 24, 2009

Related U.S. Application Data

(62) Division of application No. 10/924,375, filed on Aug. 23, 2004, now Pat. No. 7,537,928.

(60) Provisional application No. 60/497,256, filed on Aug. 22, 2003.

(51) Int. Cl.
*C12N 5/10* (2006.01)
*C12N 15/00* (2006.01)
*C12N 15/63* (2006.01)

(52) U.S. Cl. .................... 435/320.1; 435/325; 536/23.5

(58) Field of Classification Search .................. None
See application file for complete search history.

(56) References Cited

U.S. PATENT DOCUMENTS

| | | |
|---|---|---|
| 5,599,673 A | 2/1997 | Keating et al. |
| 5,858,662 A | 1/1999 | Keating et al. |
| 5,955,259 A | 9/1999 | Holmes et al. |
| 6,121,015 A | 9/2000 | O'Malley et al. |
| 6,150,357 A | 11/2000 | Salata et al. |
| 6,207,383 B1 | 3/2001 | Keating et al. |
| 6,274,332 B1 | 8/2001 | Keating et al. |
| 6,277,978 B1 | 8/2001 | Keating et al. |
| 6,323,026 B1 | 11/2001 | Keating et al. |
| 6,342,357 B1 | 1/2002 | Splawski et al. |
| 6,413,719 B1 | 7/2002 | Singh et al. |
| 6,420,124 B1 | 7/2002 | Keating et al. |
| 6,432,644 B1 | 8/2002 | Keating et al. |
| 6,451,534 B1 | 9/2002 | Keating et al. |
| 6,458,542 B1 | 10/2002 | George, Jr. et al. |
| 6,582,913 B1 | 6/2003 | Keating et al. |

OTHER PUBLICATIONS

NCBI Entrez Protein Accession No. NP_000209.potassium voltage . . . [gi:32479527] accessed on Aug. 21, 2003.
NCBI Online Mendelian Inheritance in Man; OMIM Accession No. 600163 Sodium Channel, Voltage-Gated, Type V, Alpha Subunit; SCN5A accessed on Aug. 11, 2004.
NCBI Sequence Viewer: Accession No. Q14524. Sodium Channel Protein type V alpha subunit accessed on Aug. 11, 2004.
NCBI Online Mendelian Inheritance in Man; OMIM Accession No. 152427 Potassium Channel, Voltage-Gated, SubFamily H, Member 2; KCNH2. accessed on Aug. 12, 2004.
NiceProt View of Swiss-Prot: Accession No. Q12809. accessed on Aug. 1, 2004.
NCBI Online Medelian Inheritance in Man; OMIM Assession No. 607542 Potassium Channel, Voltage-Gated. KQT-Like SubFamily, Member 1; KCNQ1. accessed on Aug. 11, 2004.
Abstract: Cardiovasc Res. Jul. 1, 2003; 59(1):27-36. A common polymorphism in KCNH2 (HERG) hastens cardiac repolarization.
Charles Antzelevitch, "Molecular Genetics of Arrhythmias and Cardiovascular Conditions Associated with Arrhythmias", PACE, vol. 26, pp. 2194-2208, (Nov. 2003).
Wever, et al., "Sudden Death in Patients Without Structural Heart Disease", J. Amer. Coll. Cardiology, vol. 43, No. 7, pp. 1137-1144, (2004).
Bellocq. et al. "Mutation in the KCNQ1 Gene Leading to the Short QT-Interval Syndrome", circulation, 109: 2394-2397, (2004).
Priori, et al., "Genetics of Cardiac Arrhythmias and Sudden Cardiac Death", Ann. N.Y. Acad. Sci., 1015: 96-110, (2004).
Gussak, et al., "ECG Phenomenon of Idiopathic and Paradoxical Short QT Internals", Cardiac Electrophysiology Review, 6: 49-53, (2002).
Charles Antzelevitch, "Molecular Genetics of Arrhythmias and Cardiovascular Conditions Associated With Arrhythmias", J. Cardiovasc Electrophysiol, 14: 1259-1272, (Nov. 2003).

*Primary Examiner*—Michael Pak
(74) *Attorney, Agent, or Firm*—Carter, DeLuca, Farrell & Schmidt, LLP

(57) ABSTRACT

Previously unknown mutations of the KCNH2, SCN5A and KCNQ1 genes are disclosed which are involved in ion channel disruptions associated with short QT syndrome, long QT syndrome, Brugada syndrome and progressive conduction disease. These mutations are utilized to diagnose and screen for short QT syndrome, long QT syndrome, Brugada syndrome and progressive conduction disease, thus providing modalities for diagnosing sudden cardiac death and/or predicting susceptibility to sudden cardiac death. Nucleic acid probes are provided which selectively hybridize to the mutant nucleic acids described herein. Antibodies are provided which selectively bind to the mutant proteins described herein. The mutations described herein are also utilized to screen for compounds useful in treating the symptoms manifest by such mutations.

3 Claims, 8 Drawing Sheets

FAMILY 30-371

FAMILY 30-335

■ SQT SYNDROME

⌀ SUDDEN DEATH

C1764A
N588K
FAMILY 30-371

C1764G
N588K
FAMILY 30-335

WILD TYPE

Effect of Sotalol in HEK Cells (Mutant v. Wild Type KCNH2)

Effect of Quinidine in HEK Cells (Mutant v. Wild Type KCNH2)

SEQUENCE LISTING

<160> NUMBER OF SEQ ID NOS: 134

<210> SEQ ID NO 1
<211> LENGTH: 581
<212> TYPE: PRT
<213> ORGANISM: homo sapiens

<400> SEQUENCE: 1

```
Met Glu Thr Arg Gly Ser Arg Leu Thr Gly Gly Gln Gly Arg Val Tyr
1               5                   10                  15

Asn Phe Leu Glu Arg Pro Thr Gly Trp Lys Cys Phe Val Tyr His Phe
            20                  25                  30

Ala Val Phe Leu Ile Val Leu Val Cys Leu Ile Phe Ser Val Leu Ser
        35                  40                  45

Thr Ile Glu Gln Tyr Ala Ala Leu Ala Thr Gly Thr Leu Phe Trp Met
    50                  55                  60

Glu Ile Val Leu Val Val Phe Phe Gly Thr Glu Tyr Val Val Arg Leu
65                  70                  75                  80

Trp Ser Ala Gly Cys Arg Ser Lys Tyr Val Gly Leu Trp Gly Arg Leu
                85                  90                  95

Arg Phe Ala Arg Lys Pro Ile Ser Ile Ile Asp Leu Ile Val Val Val
            100                 105                 110
```

```
Ala Ser Met Val Val Leu Cys Val Gly Ser Lys Gly Gln Val Phe Ala
        115                 120                 125

Thr Ser Ala Ile Arg Gly Ile Arg Phe Leu Gln Ile Leu Arg Met Leu
130                 135                 140

His Val Asp Arg Gln Gly Gly Thr Trp Arg Leu Gly Ser Val Val
145                 150                 155                 160

Phe Ile His Arg Gln Glu Leu Ile Thr Thr Leu Tyr Ile Gly Phe Leu
                165                 170                 175

Gly Leu Ile Phe Ser Ser Tyr Phe Val Tyr Leu Ala Glu Lys Asp Ala
                180                 185                 190

Val Asn Glu Ser Gly Arg Val Glu Phe Gly Ser Tyr Ala Asp Ala Leu
                195                 200                 205

Trp Trp Gly Val Val Thr Val Thr Thr Ile Gly Tyr Gly Asp Lys Val
        210                 215                 220

Pro Gln Thr Trp Val Gly Lys Thr Ile Ala Ser Cys Phe Ser Val Phe
225                 230                 235                 240

Ala Ile Ser Phe Phe Ala Leu Pro Ala Gly Ile Leu Gly Ser Gly Phe
                245                 250                 255

Ala Leu Lys Val Gln Gln Lys Gln Arg Gln Lys His Phe Asn Arg Gln
                260                 265                 270

Ile Pro Ala Ala Ala Ser Leu Ile Gln Thr Ala Trp Arg Cys Tyr Ala
                275                 280                 285

Ala Glu Asn Pro Asp Ser Ser Thr Trp Lys Ile Tyr Ile Arg Lys Ala
                290                 295                 300

Pro Arg Ser His Thr Leu Leu Ser Pro Ser Pro Lys Pro Lys Lys Ser
305                 310                 315                 320

Val Val Val Lys Lys Lys Phe Lys Leu Asp Lys Asp Asn Gly Val
                325                 330                 335

Thr Pro Gly Glu Lys Met Leu Thr Val Pro His Ile Thr Cys Asp Pro
                340                 345                 350

Pro Glu Glu Arg Arg Leu Asp His Phe Ser Val Asp Gly Tyr Asp Ser
                355                 360                 365

Ser Val Arg Lys Ser Pro Thr Leu Leu Glu Val Ser Met Pro His Phe
        370                 375                 380

Met Arg Thr Asn Ser Phe Ala Glu Asp Leu Asp Leu Glu Gly Glu Thr
385                 390                 395                 400

Leu Leu Thr Pro Ile Thr His Ile Ser Gln Leu Arg Glu His His Arg
                405                 410                 415

Ala Thr Ile Lys Val Ile Arg Arg Met Gln Tyr Phe Val Ala Lys Lys
                420                 425                 430

Lys Phe Gln Gln Ala Arg Lys Pro Tyr Asp Val Arg Asp Val Ile Glu
                435                 440                 445

Gln Tyr Ser Gln Gly His Leu Asn Leu Met Val Arg Ile Lys Glu Leu
        450                 455                 460

Gln Arg Arg Leu Asp Gln Ser Ile Gly Lys Pro Ser Leu Phe Ile Ser
465                 470                 475                 480

Val Ser Glu Lys Ser Lys Asp Arg Gly Ser Asn Thr Ile Gly Ala Arg
                485                 490                 495

Leu Asn Arg Val Glu Asp Lys Val Thr Gln Leu Asp Gln Arg Leu Ala
                500                 505                 510

Leu Ile Thr Asp Met Leu His Gln Leu Leu Ser Leu His Gly Gly Ser
        515                 520                 525

Thr Pro Gly Ser Gly Gly Pro Pro Arg Glu Gly Gly Ala His Ile Thr
```

```
            530             535             540
Gln Pro Cys Gly Ser Gly Gly Ser Val Asp Pro Glu Leu Phe Leu Pro
545                 550                 555                 560

Ser Asn Thr Leu Pro Thr Tyr Glu Gln Leu Thr Val Pro Arg Arg Gly
                565                 570                 575

Pro Asp Glu Gly Ser
            580

<210> SEQ ID NO 2
<211> LENGTH: 1746
<212> TYPE: DNA
<213> ORGANISM: homo sapiens

<400> SEQUENCE: 2
atggagacgc gcgggtctag gctcaccggc ggccagggcc gcgtctacaa cttcctcgag      60
cgtcccaccg gctggaaatg cttcgtttac cacttcgccg tcttcctcat cgtcctggtc     120
tgcctcatct tcagcgtgct gtccaccatc gagcagtatg ccgccctggc cacggggact     180
ctcttctgga tggagatcgt gctggtggtg ttcttcggga cggagtacgt ggtccgcctc     240
tggtccgccg gctgccgcag caagtacgtg ggcctctggg ggcggctgcg ctttgcccgg     300
aagcccattt ccatcatcga cctcatcgtg gtcgtggcct ccatggtggt cctctgcgtg     360
ggctccaagg ggcaggtgtt tgccacgtcg gccatcaggg gcatccgctt cctgcagatc     420
ctgaggatgc tacacgtcga ccgccaggga ggcacctgga ggctcctggg ctccgtggtc     480
ttcatccacc gccaggagct gataaccacc ctgtacatcg gcttcctggg cctcatcttc     540
tcctcgtact tgtgtacct ggctgagaag gacgcggtga acgagtcagg ccgcgtggag     600
ttcggcagct acgcagatgc gctgtggtgg ggggtggtca cagtcaccac catcggctat     660
ggggacaagg tgccccagac gtgggtcggg aagaccatcg cctcctgctt ctctgtcttt     720
gccatctcct tctttgcgct cccagcgggg attcttggct cggggtttgc cctgaaggtg     780
cagcagaagc agaggcagaa gcacttcaac cggcagatcc cggcggcagc ctcactcatt     840
cagaccgcat ggaggtgcta tgctgccgag aaccccgact cctccacctg gaagatctac     900
atccggaagg ccccccggag ccacactctg ctgtcaccca gccccaaacc caagaagtct     960
gtggtggtaa agaaaaaaaa gttcaagctg acaaagaca atggggtgac tcctggagag    1020
aagatgctca cagtccccca tatcacgtgc gacccccag aagagcggcg gctggaccac    1080
ttctctgtcg acggctatga cagttctgta aggaagagcc caacactgct ggaagtgagc    1140 atgcccccatt tcatgagaac caacagcttc gccgaggacc tggacctgga aggggagact    1200
ctgctgacac ccatcaccca catctcacag ctgcgggaac accatcgggc caccattaag    1260
gtcattcgac gcatgcagta ctttgtggcc aagaagaaat ccagcaagc gcggaagcct    1320 tacgatgtgc gggacgtcat tgagcagtac tcgcagggcc acctcaacct catggtgcgc    1380
atcaaggagc tgcagaggag gctggaccag tccattggga agccctcact gttcatctcc    1440
gtctcagaaa agagcaagga tcgcggcagc aacacgatcg cgcccgcct gaaccgagta    1500 gaagacaagg tgacgcagct ggaccagagg ctggcactca tcaccgacat gcttcaccag    1560
ctgctctcct tgcacggtgg cagcaccccc ggcagcggcg gccccccag agagggcggg    1620 gcccacatca cccagccctg cggcagtggc ggctccgtcg accctgagct cttcctgccc    1680
agcaacaccc tgcccaccta cgagcagctg accgtgccca ggggggccc cgatgagggg    1740 tcctga                                                              1746
```

<210> SEQ ID NO 3
<211> LENGTH: 2015
<212> TYPE: PRT
<213> ORGANISM: homo sapiens

<400> SEQUENCE: 3

Met Ala Asn Phe Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

```
Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Lys Glu Lys
                420                 425                 430

Arg Phe Gln Glu Ala Met Glu Met Leu Lys Lys Glu His Glu Ala Leu
                435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
                500                 505                 510

Arg Gly Leu Ser Arg Thr Ser Met Lys Pro Arg Ser Ser Arg Gly Ser
                515                 520                 525

Ile Phe Thr Phe Arg Arg Arg Asp Leu Gly Ser Glu Ala Asp Phe Ala
                530                 535                 540

Asp Asp Glu Asn Ser Thr Ala Gly Glu Ser Glu Ser His His Ala Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
                580                 585                 590

Ser Thr Val Asp Cys Asn Gly Val Val Ser Leu Leu Gly Ala Gly Asp
                595                 600                 605

Pro Glu Ala Thr Ser Pro Gly Ser His Leu Leu Arg Pro Val Met Leu
                610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
                660                 665                 670

Leu Glu Glu Leu Glu Glu Ser Arg His Lys Cys Pro Pro Cys Trp Asn
                675                 680                 685

Arg Leu Ala Gln Arg Tyr Leu Ile Trp Glu Cys Cys Pro Leu Trp Met
690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
                740                 745                 750

Asn Leu Val Phe Thr Gly Ile Phe Thr Ala Glu Met Thr Phe Lys Ile
                755                 760                 765

Ile Ala Leu Asp Pro Tyr Tyr Tyr Phe Gln Gln Gly Trp Asn Ile Phe
                770                 775                 780

Asp Ser Ile Ile Val Ile Leu Ser Leu Met Glu Leu Gly Leu Ser Arg
785                 790                 795                 800
```

-continued

```
Met Ser Asn Leu Ser Val Leu Arg Ser Phe Arg Leu Arg Val Phe
                805                 810                 815

Lys Leu Ala Lys Ser Trp Pro Thr Leu Asn Thr Leu Ile Lys Ile Ile
                820                 825                 830

Gly Asn Ser Val Gly Ala Leu Gly Asn Leu Thr Leu Val Leu Ala Ile
                835                 840                 845

Ile Val Phe Ile Phe Ala Val Val Gly Met Gln Leu Phe Gly Lys Asn
            850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
                900                 905                 910

Ser Leu Cys Leu Leu Val Phe Leu Leu Val Met Val Ile Gly Asn Leu
                915                 920                 925

Val Val Leu Asn Leu Phe Leu Ala Leu Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
                980                 985                 990

Ala Ala Leu Ala Ala Gln Gly Gln Leu Pro Ser Cys Ile Ala Thr Pro
            995                 1000                1005

Tyr Ser Pro Pro Pro Pro Glu Thr Glu Lys Val Pro Pro Thr Arg
            1010                1015                1020

Lys Glu Thr Arg Phe Glu Glu Gly Glu Gln Pro Gly Gln Gly Thr
            1025                1030                1035

Pro Gly Asp Pro Glu Pro Val Cys Val Pro Ile Ala Val Ala Glu
            1040                1045                1050

Ser Asp Thr Asp Asp Gln Glu Glu Asp Glu Glu Asn Ser Leu Gly
            1055                1060                1065

Thr Glu Glu Glu Ser Ser Lys Gln Glu Ser Gln Pro Val Ser Gly
            1070                1075                1080

Gly Pro Glu Ala Pro Pro Asp Ser Arg Thr Trp Ser Gln Val Ser
            1085                1090                1095

Ala Thr Ala Ser Ser Glu Ala Glu Ala Ser Ala Ser Gln Ala Asp
            1100                1105                1110

Trp Arg Gln Gln Trp Lys Ala Glu Pro Gln Ala Pro Gly Cys Gly
            1115                1120                1125

Glu Thr Pro Glu Asp Ser Cys Ser Glu Gly Ser Thr Ala Asp Met
            1130                1135                1140

Thr Asn Thr Ala Glu Leu Leu Glu Gln Ile Pro Asp Leu Gly Gln
            1145                1150                1155

Asp Val Lys Asp Pro Glu Asp Cys Phe Thr Glu Gly Cys Val Arg
            1160                1165                1170

Arg Cys Pro Cys Cys Ala Val Asp Thr Thr Gln Ala Pro Gly Lys
            1175                1180                1185

Val Trp Trp Arg Leu Arg Lys Thr Cys Tyr His Ile Val Glu His
            1190                1195                1200

Ser Trp Phe Glu Thr Phe Ile Ile Phe Met Ile Leu Leu Ser Ser
```

-continued

```
            1205                1210                1215
Gly Ala Leu Ala Phe Glu Asp Ile Tyr Leu Glu Trp Lys Thr
    1220                1225                1230
Ile Lys Val Leu Leu Glu Tyr Ala Asp Lys Met Phe Thr Tyr Val
    1235                1240                1245
Phe Val Leu Glu Met Leu Leu Lys Trp Val Ala Tyr Gly Phe Lys
    1250                1255                1260
Lys Tyr Phe Thr Asn Ala Trp Cys Trp Leu Asp Phe Leu Ile Val
    1265                1270                1275
Asp Val Ser Leu Val Ser Leu Val Ala Asn Thr Leu Gly Phe Ala
    1280                1285                1290
Glu Met Gly Pro Ile Lys Ser Leu Arg Thr Leu Arg Ala Leu Arg
    1295                1300                1305
Pro Leu Arg Ala Leu Ser Arg Phe Glu Gly Met Arg Val Val Val
    1310                1315                1320
Asn Ala Leu Val Gly Ala Ile Pro Ser Ile Met Asn Val Leu Leu
    1325                1330                1335
Val Cys Leu Ile Phe Trp Leu Ile Phe Ser Ile Met Gly Val Asn
    1340                1345                1350
Leu Phe Ala Gly Lys Phe Gly Arg Cys Ile Asn Gln Thr Glu Gly
    1355                1360                1365
Asp Leu Pro Leu Asn Tyr Thr Ile Val Asn Asn Lys Ser Gln Cys
    1370                1375                1380
Glu Ser Leu Asn Leu Thr Gly Glu Leu Tyr Trp Thr Lys Val Lys
    1385                1390                1395
Val Asn Phe Asp Asn Val Gly Ala Gly Tyr Leu Ala Leu Leu Gln
    1400                1405                1410
Val Ala Thr Phe Lys Gly Trp Met Asp Ile Met Tyr Ala Ala Val
    1415                1420                1425
Asp Ser Arg Gly Tyr Glu Glu Gln Pro Gln Trp Glu Tyr Asn Leu
    1430                1435                1440
Tyr Met Tyr Ile Tyr Phe Val Ile Phe Ile Ile Phe Gly Ser Phe
    1445                1450                1455
Phe Thr Leu Asn Leu Phe Ile Gly Val Ile Ile Asp Asn Phe Asn
    1460                1465                1470
Gln Gln Lys Lys Lys Leu Gly Gly Gln Asp Ile Phe Met Thr Glu
    1475                1480                1485
Glu Gln Lys Lys Tyr Tyr Asn Ala Met Lys Lys Leu Gly Ser Lys
    1490                1495                1500
Lys Pro Gln Lys Pro Ile Pro Arg Pro Leu Asn Lys Tyr Gln Gly
    1505                1510                1515
Phe Ile Phe Asp Ile Val Thr Lys Gln Ala Phe Asp Val Thr Ile
    1520                1525                1530
Met Phe Leu Ile Cys Leu Asn Met Val Thr Met Met Val Glu Thr
    1535                1540                1545
Asp Asp Gln Ser Pro Glu Lys Ile Asn Ile Leu Ala Lys Ile Asn
    1550                1555                1560
Leu Leu Phe Val Ala Ile Phe Thr Gly Glu Cys Ile Val Lys Leu
    1565                1570                1575
Ala Ala Leu Arg His Tyr Tyr Phe Thr Asn Ser Trp Asn Ile Phe
    1580                1585                1590
Asp Phe Val Val Val Ile Leu Ser Ile Val Gly Thr Val Leu Ser
    1595                1600                1605
```

```
Asp Ile Ile Gln Lys Tyr Phe Phe Ser Pro Thr Leu Phe Arg Val
1610                1615                1620

Ile Arg Leu Ala Arg Ile Gly Arg Ile Leu Arg Leu Ile Arg Gly
    1625            1630                1635

Ala Lys Gly Ile Arg Thr Leu Leu Phe Ala Leu Met Met Ser Leu
1640                1645                1650

Pro Ala Leu Phe Asn Ile Gly Leu Leu Leu Phe Leu Val Met Phe
    1655            1660                1665

Ile Tyr Ser Ile Phe Gly Met Ala Asn Phe Ala Tyr Val Lys Trp
1670                1675                1680

Glu Ala Gly Ile Asp Asp Met Phe Asn Phe Gln Thr Phe Ala Asn
    1685            1690                1695

Ser Met Leu Cys Leu Phe Gln Ile Thr Thr Ser Ala Gly Trp Asp
1700                1705                1710

Gly Leu Leu Ser Pro Ile Leu Asn Thr Gly Pro Pro Tyr Cys Asp
    1715            1720                1725

Pro Thr Leu Pro Asn Ser Asn Gly Ser Arg Gly Asp Cys Gly Ser
1730                1735                1740

Pro Ala Val Gly Ile Leu Phe Phe Thr Thr Tyr Ile Ile Ile Ser
    1745            1750                1755

Phe Leu Ile Val Val Asn Met Tyr Ile Ala Ile Ile Leu Glu Asn
1760                1765                1770

Phe Ser Val Ala Thr Glu Glu Ser Thr Glu Pro Leu Ser Glu Asp
    1775            1780                1785

Asp Phe Asp Met Phe Tyr Glu Ile Trp Glu Lys Phe Asp Pro Glu
1790                1795                1800

Ala Thr Gln Phe Ile Glu Tyr Ser Val Leu Ser Asp Phe Ala Asp
    1805            1810                1815

Ala Leu Ser Glu Pro Leu Arg Ile Ala Lys Pro Asn Gln Ile Ser
1820                1825                1830

Leu Ile Asn Met Asp Leu Pro Met Val Ser Gly Asp Arg Ile His
    1835            1840                1845

Cys Met Asp Ile Leu Phe Ala Phe Thr Lys Arg Val Leu Gly Glu
1850                1855                1860

Ser Gly Glu Met Asp Ala Leu Lys Ile Gln Met Glu Glu Lys Phe
    1865            1870                1875

Met Ala Ala Asn Pro Ser Lys Ile Ser Tyr Glu Pro Ile Thr Thr
1880                1885                1890

Thr Leu Arg Arg Lys His Glu Glu Val Ser Ala Met Val Ile Gln
    1895            1900                1905

Arg Ala Phe Arg Arg His Leu Leu Gln Arg Ser Leu Lys His Ala
1910                1915                1920

Ser Phe Leu Phe Arg Gln Gln Ala Gly Ser Gly Leu Ser Glu Glu
    1925            1930                1935

Asp Ala Pro Glu Arg Glu Gly Leu Ile Ala Tyr Val Met Ser Glu
1940                1945                1950

Asn Phe Ser Arg Pro Leu Gly Pro Pro Ser Ser Ser Ser Ile Ser
    1955            1960                1965

Ser Thr Ser Phe Pro Pro Ser Tyr Asp Ser Val Thr Arg Ala Thr
1970                1975                1980

Ser Asp Asn Leu Gln Val Arg Gly Ser Asp Tyr Ser His Ser Glu
    1985            1990                1995
```

```
Asp Leu Ala Asp Phe Pro Pro  Ser Pro Asp Arg Asp  Arg Glu Ser
    2000             2005              2010

Ile Val
    2015

<210> SEQ ID NO 4
<211> LENGTH: 6048
<212> TYPE: DNA
<213> ORGANISM: homo sapiens

<400> SEQUENCE: 4
atggcaaact tcctattacc tcggggcacc agcagcttcc gcaggttcac acgggagtcc      60
ctggcagcca tcgagaagcg catggcggag aagcaagccc gcggctcaac caccttgcag     120
gagagccgag aggggctgcc cgaggaggag gctccccggc cccagctgga cctgcaggcc     180
tccaaaaagc tgccagatct ctatggcaat ccaccccaag agctcatcgg agagcccctg     240
gaggacctgg acccccttcta tagcacccaa aagactttca tcgtactgaa taaaggcaag     300
accatcttcc ggttcagtgc caccaacgcc ttgtatgtcc tcagtcccctt ccaccccatc     360 cggagagcgg ctgtgaagat tctggttcac tcgctcttca acatgctcat catgtgcacc     420
atcctcacca actgcgtgtt catggcccag cacgaccctc caccctggac caagtatgtc     480
gagtacacct tcaccgccat ttacaccttt gagtctctgg tcaagattct ggctcgaggc     540
ttctgcctgc acgcgttcac tttccttcgg gacccatgga actggctgga ctttagtgtg     600
attatcatgg catacacaac tgaatttgtg gacctgggca atgtctcagc cttacgcacc     660
ttccgagtcc tccgggccct gaaaactata tcagtcattt cagggctgaa gaccatcgtg     720
ggggccctga tccagtctgt gaagaagctg gctgatgtga tggtcctcac agtcttctgc     780
ctcagcgtct ttgccctcat cggcctgcag ctcttcatgg gcaacctaag gcacaagtgc     840
gtgcgcaact tcacagcgct caacggcacc aacggctccg tggaggccga cggcttggtc     900
tgggaatccc tggaccttta cctcagtgat ccagaaaatt acctgctcaa gaacggcacc     960
tctgatgtgt tactgtgtgg gaacagctct gacgctggga catgtccgga gggctaccgg    1020
tgcctaaagg caggcgagaa ccccgaccac ggctacacca gcttcgattc ctttgcctgg    1080
gcctttcttg cactcttccg cctgatgacg caggactgct gggagcgcct ctatcagcag    1140
accctcaggt ccgcagggaa gatctacatg atcttcttca tgcttgtcat cttcctgggg    1200
tccttctacc tggtgaacct gatcctggcc gtggtcgcaa tggcctatga ggagcaaaac    1260
caagccacca tcgctgagac cgaggagaag gaaaagcgct tccaggaggc catggaaatg    1320
ctcaagaaag aacacgaggc cctcaccatc aggggtgtgg ataccgtgtc ccgtagctcc    1380
ttggagatgt ccccttttggc cccagtaaac agccatgaga aagaagcaa gaggagaaaa    1440 cggatgtctt caggaactga ggagtgtggg aggacaggc tccccaagtc tgactcagaa    1500
gatggtccca gagcaatgaa tcatctcagc ctcacccgtg gcctcagcag acttctatg    1560 aagccacgtt ccagccgcgg gagcattttc acctttcgca ggcgagacct gggttctgaa    1620
gcagattttg cagatgatga aaacagcaca gcggggggaga gcgagagcca ccacgcatca    1680
ctgctggtgc cctggcccct cgccggacc agtgcccagg gacagcccag tcccggaacc    1740
tcggctcctg gccacgccct ccatggcaaa agaacagca ctgtggactg caatgggtg    1800 gtctcattac tgggggcagg cgacccagag gccacatccc caggaagcca cctcctccgc    1860
cctgtgatgc tagagcaccc gccagacacg accacgccat cggaggagcc aggcgggccc    1920
cagatgctga acctcccagg ctccgtgtgta gatggcttcg aggagccagg agcacggcag    1980
```

```
cgggccctca gcgcagtcag cgtcctcacc agcgcactgg aagagttaga ggagtctcgc    2040
cataagtgtc caccatgctg gaaccgtctc gcccagcgct acctgatctg ggagtgctgc    2100
ccgctgtgga tgtccatcaa gcagggagtg aagttggtgg tcatggaccc gtttactgac    2160
ctcaccatca ctatgtgcat cgtactcaac acactcttca tggcgctgga gcactacaac    2220
atgacaagtg aattcgagga gatgctgcag gtcggaaacc tggtcttcac agggattttc    2280
acagcagaga tgaccttcaa gatcattgcc ctcgacccct actactactt ccaacagggc    2340
tggaacatct tcgacagcat catcgtcatc cttagcctca tggagctggg cctgtcccgc    2400
atgagcaact tgtcggtgct gcgctccttc cgcctgctgc gggtcttcaa gctggccaaa    2460
tcatggccca ccctgaacac actcatcaag atcatcggga actcagtggg ggcactgggg    2520
aacctgacac tggtgctagc catcatcgtg ttcatctttg ctgtggtggg catgcagctc    2580
tttggcaaga actactcgga gctgagggac agcgactcag gcctgctgcc tcgctggcac    2640
atgatggact tctttcatgc cttcctcatc atcttccgca tcctctgtgg agagtggatc    2700
gagaccatgt gggactgcat ggaggtgtcg gggcagtcat tatgcctgct ggtcttcttg    2760
cttgttatgg tcattggcaa ccttgtggtc ctgaatctct tcctggcctt gctgctcagc    2820
tccttcagtg cagacaacct cacagccccc gatgaggaca gagagatgaa caacctccag    2880
ctggccctgg cccgcatcca gagggcctg cgctttgtca gcggaccac ctgggatttc     2940 tgctgtggtc tcctgcggca gcggcctcag aagcccgcag cccttgccgc ccagggccag    3000
ctgcccagct gcattgccac ccctactcc cgccacccc cagagacgga gaaggtgcct     3060
cccacccgca aggaaacacg gtttgaggaa ggcgagcaac caggccaggg caccccgggg    3120
gatccagagc ccgtgtgtgt gcccatcgct gtggccgagt cagacacaga tgaccaagaa    3180
gaagatgagg agaacagcct gggcacggag gaggagtcca gcaagcagga atcccagcct    3240
gtgtccggtg cccagaggc ccctccggat tccaggacct ggagccaggt gtcagcgact    3300
gcctcctctg aggccgaggc cagtgcatct caggccgact ggcggcagca gtggaaagcg    3360
gaaccccagg ccccagggtg cggtgagacc ccagaggaca gttgctccga gggcagcaca    3420
gcagacatga ccaacaccgc tgagctcctg gagcagatcc ctgacctcgg ccaggatgtc    3480
aaggacccag aggactgctt cactgaaggc tgtgtccggc gctgtccctg ctgtgcggtg    3540
gacaccacac aggccccagg gaaggtctgg tggcggttgc gcaagacctg ctaccacatc    3600
gtggagcaca gctggttcga gacattcatc atcttcatga tcctactcag cagtggagcg    3660
ctggccttcg aggacatcta cctagaggag tggaagacca tcaaggttct gcttgagtat    3720
gccgacaaga tgttcacata tgtcttcgtg ctggagatgc tgctcaagtg ggtggcctac    3780
ggcttcaaga agtacttcac caatgcctgg tgctggctcg acttcctcat cgtagacgtc    3840
tctctggtca gcctggtggc caacaccctg ggctttgccg agatgggccc catcaagtca    3900
ctgcggacgc tgcgtgcact ccgtcctctg agagctctgt cacgatttga gggcatgagg    3960
gtggtggtca atgccctggt gggcgccatc ccgtccatca tgaacgtcct cctcgtctgc    4020
ctcatcttct ggctcatctt cagcatcatg ggcgtgaacc tctttgcggg gaagtttggg    4080
aggtgcatca accagacaga gggagacttg ccttttgaact acaccatcgt gaacaacaag    4140
agccagtgtg agtccttgaa cttgaccgga gaattgtact ggaccaaggt gaaagtcaac    4200
tttgacaacg tgggggccgg gtacctggcc cttctgcagg tggcaacatt taaaggctgg    4260
atggacatta tgtatgcagc tgtggactcc aggggtatg aagagcagcc tcagtgggaa    4320
```

```
tacaacctct acatgtacat ctattttgtc attttcatca tctttgggtc tttcttcacc    4380
ctgaacctct ttattggtgt catcattgac aacttcaacc aacagaagaa aaagttaggg    4440
ggccaggaca tcttcatgac agaggagcag aagaagtact acaatgccat gaagaagctg    4500
ggctccaaga agccccagaa gcccatccca cggcccctga acaagtacca gggcttcata    4560
ttcgacattg tgaccaagca ggcctttgac gtcaccatca tgtttctgat ctgcttgaat    4620
atggtgacca tgatggtgga gacagatgac caaagtcctg agaaaatcaa catcttggcc    4680
aagatcaacc tgctctttgt ggccatcttc acaggcgagt gtattgtcaa gctggctgcc    4740
ctgcgccact actacttcac caacagctgg aatatcttcg acttcgtggt tgtcatcctc    4800
tccatcgtgg gcactgtgct ctcggacatc atccagaagt acttcttctc cccgacgctc    4860
ttccgagtca tccgcctggc ccgaataggc cgcatcctca gactgatccg aggggccaag    4920
gggatccgca cgctgctctt tgccctcatg atgtccctgc ctgccctctt caacatcggg    4980
ctgctgctct tcctcgtcat gttcatctac tccatctttg gcatggccaa cttcgcttat    5040
gtcaagtggg aggctggcat cgacgacatg ttcaacttcc agaccttcgc caacagcatg    5100
ctgtgcctct tccagatcac cacgtcggcc ggctgggatg cctcctcag ccccatcctc     5160
aacactgggc cgccctactg cgaccccact ctgcccaaca gcaatggctc tcgggggac     5220
tgcgggagcc cagccgtggg catcctcttc ttcaccacct acatcatcat ctccttcctc    5280
atcgtggtca acatgtacat tgccatcatc ctggagaact cagcgtggc cacggaggag     5340
agcaccgagc ccttaagtga ggacgacttc gatatgttct atgagatctg ggagaaattt    5400
gacccagagg ccactcagtt tattgagtat tcggtcctgt ctgactttgc cgatgccctg    5460
tctgagccac tccgtatcgc caagcccaac cagataagcc tcatcaacat ggacctgccc    5520
atggtgagtg gggaccgcat ccattgcatg gacattctct ttgccttcac caaaagggtc    5580
ctggggggagt ctggggagat ggacgccctg aagatccaga tggaggagaa gttcatggca   5640
gccaacccat ccaagatctc ctacgagccc atcaccacca cactccggcg caagcacgaa    5700
gaggtgtcgg ccatggttat ccagagagcc ttccgcaggc acctgctgca acgctctttg    5760
aagcatgcct ccttcctctt ccgtcagcag gcgggcagcg gcctctccga agaggatgcc    5820
cctgagcgag agggcctcat cgcctacgtg atgagtgaga acttctcccg acccctttggc   5880
ccaccctcca gctcctccat ctcctccact tccttcccac cctcctatga cagtgtcact    5940
agagccacca gcgataacct ccaggtgcgg gggtctgact acagccacag tgaagatctc    6000
gccgacttcc ccccttctcc ggacagggac cgtgagtcca tcgtgtga                 6048
```

<210> SEQ ID NO 5
<211> LENGTH: 1159
<212> TYPE: PRT
<213> ORGANISM: homo sapiens

<400> SEQUENCE: 5

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
                20                  25                  30

Asn Ala Arg Val Glu Asn Cys Ala Val Ile Tyr Cys Asn Asp Gly Phe
            35                  40                  45

Cys Glu Leu Cys Gly Tyr Ser Arg Ala Glu Val Met Gln Arg Pro Cys
        50                  55                  60

Thr Cys Asp Phe Leu His Gly Pro Arg Thr Gln Arg Arg Ala Ala Ala
```

-continued

```
                65                  70                  75                  80
Gln Ile Ala Gln Ala Leu Leu Gly Ala Glu Glu Arg Lys Val Glu Ile
                    85                  90                  95
Ala Phe Tyr Arg Lys Asp Gly Ser Cys Phe Leu Cys Leu Val Asp Val
                100                 105                 110
Val Pro Val Lys Asn Glu Asp Gly Ala Val Ile Met Phe Ile Leu Asn
                115                 120                 125
Phe Glu Val Val Met Glu Lys Asp Met Val Gly Ser Pro Ala His Asp
            130                 135                 140
Thr Asn His Arg Gly Pro Pro Thr Ser Trp Leu Ala Pro Gly Arg Ala
145                 150                 155                 160
Lys Thr Phe Arg Leu Lys Leu Pro Ala Leu Leu Ala Leu Thr Ala Arg
                165                 170                 175
Glu Ser Ser Val Arg Ser Gly Ala Gly Gly Ala Gly Ala Pro Gly
                180                 185                 190
Ala Val Val Val Asp Val Asp Leu Thr Pro Ala Ala Pro Ser Ser Glu
                195                 200                 205
Ser Leu Ala Leu Asp Glu Val Thr Ala Met Asp Asn His Val Ala Gly
            210                 215                 220
Leu Gly Pro Ala Glu Glu Arg Arg Ala Leu Val Gly Pro Gly Ser Pro
225                 230                 235                 240
Pro Arg Ser Ala Pro Gly Gln Leu Pro Ser Pro Arg Ala His Ser Leu
                245                 250                 255
Asn Pro Asp Ala Ser Gly Ser Ser Cys Ser Leu Ala Arg Thr Arg Ser
                260                 265                 270
Arg Glu Ser Cys Ala Ser Val Arg Arg Ala Ser Ser Ala Asp Asp Ile
                275                 280                 285
Glu Ala Met Arg Ala Gly Val Leu Pro Pro Pro Arg His Ala Ser
            290                 295                 300
Thr Gly Ala Met His Pro Leu Arg Ser Gly Leu Leu Asn Ser Thr Ser
305                 310                 315                 320
Asp Ser Asp Leu Val Arg Tyr Arg Thr Ile Ser Lys Ile Pro Gln Ile
                325                 330                 335
Thr Leu Asn Phe Val Asp Leu Lys Gly Asp Pro Phe Leu Ala Ser Pro
                340                 345                 350
Thr Ser Asp Arg Glu Ile Ile Ala Pro Lys Ile Lys Glu Arg Thr His
                355                 360                 365
Asn Val Thr Glu Lys Val Thr Gln Val Leu Ser Leu Gly Ala Asp Val
            370                 375                 380
Leu Pro Glu Tyr Lys Leu Gln Ala Pro Arg Ile His Arg Trp Thr Ile
385                 390                 395                 400
Leu His Tyr Ser Pro Phe Lys Ala Val Trp Asp Trp Leu Ile Leu Leu
                405                 410                 415
Leu Val Ile Tyr Thr Ala Val Phe Thr Pro Tyr Ser Ala Ala Phe Leu
                420                 425                 430
Leu Lys Glu Thr Glu Glu Gly Pro Pro Ala Thr Glu Cys Gly Tyr Ala
                435                 440                 445
Cys Gln Pro Leu Ala Val Val Asp Leu Ile Val Asp Ile Met Phe Ile
                450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
```

-continued

```
Trp Phe Leu Ile Asp Met Val Ala Ala Ile Pro Phe Asp Leu Leu Ile
            500                 505                 510
Phe Gly Ser Gly Ser Glu Glu Leu Ile Gly Leu Leu Lys Thr Ala Arg
        515                 520                 525
Leu Leu Arg Leu Val Arg Val Ala Arg Lys Leu Asp Arg Tyr Ser Glu
    530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
            565                 570                 575
Pro His Met Asp Ser Arg Ile Gly Trp Leu His Asn Leu Gly Asp Gln
        580                 585                 590
Ile Gly Lys Pro Tyr Asn Ser Gly Leu Gly Gly Pro Ser Ile Lys
    595                 600                 605
Asp Lys Tyr Val Thr Ala Leu Tyr Phe Thr Phe Ser Ser Leu Thr Ser
    610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
            660                 665                 670
Tyr His Thr Gln Met Leu Arg Val Arg Glu Phe Ile Arg Phe His Gln
        675                 680                 685
Ile Pro Asn Pro Leu Arg Gln Arg Leu Glu Glu Tyr Phe Gln His Ala
    690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
            740                 745                 750
Ala Leu Ala Met Lys Phe Lys Thr Thr His Ala Pro Pro Gly Asp Thr
        755                 760                 765
Leu Val His Ala Gly Asp Leu Leu Thr Ala Leu Tyr Phe Ile Ser Arg
    770                 775                 780
Gly Ser Ile Glu Ile Leu Arg Gly Asp Val Val Val Ala Ile Leu Gly
785                 790                 795                 800
Lys Asn Asp Ile Phe Gly Glu Pro Leu Asn Leu Tyr Ala Arg Pro Gly
                805                 810                 815
Lys Ser Asn Gly Asp Val Arg Ala Leu Thr Tyr Cys Asp Leu His Lys
            820                 825                 830
Ile His Arg Asp Asp Leu Leu Glu Val Leu Asp Met Tyr Pro Glu Phe
        835                 840                 845
Ser Asp His Phe Trp Ser Ser Leu Glu Ile Thr Phe Asn Leu Arg Asp
    850                 855                 860
Thr Asn Met Ile Pro Gly Ser Pro Gly Ser Thr Glu Leu Glu Gly Gly
865                 870                 875                 880
Phe Ser Arg Gln Arg Lys Arg Lys Leu Ser Phe Arg Arg Thr Asp
                885                 890                 895
Lys Asp Thr Glu Gln Pro Gly Glu Val Ser Ala Leu Gly Pro Gly Arg
            900                 905                 910
```

```
Ala Gly Ala Gly Pro Ser Ser Arg Gly Arg Pro Gly Pro Trp Gly
        915                 920                 925

Glu Ser Pro Ser Ser Gly Pro Ser Ser Pro Glu Ser Ser Glu Asp Glu
        930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                    965                 970                 975

Cys Glu Lys Ser Ser Asp Thr Cys Asn Pro Leu Ser Gly Ala Phe Ser
                980                 985                 990

Gly Val Ser Asn Ile Phe Ser Phe Trp Gly Asp Ser Arg Gly Arg Gln
        995                 1000                1005

Tyr Gln Glu Leu Pro Arg Cys Pro Ala Pro Thr Pro Ser Leu Leu
        1010                1015                1020

Asn Ile Pro Leu Ser Ser Pro Gly Arg Arg Pro Arg Gly Asp Val
        1025                1030                1035

Glu Ser Arg Leu Asp Ala Leu Gln Arg Gln Leu Asn Arg Leu Glu
        1040                1045                1050

Thr Arg Leu Ser Ala Asp Met Ala Thr Val Leu Gln Leu Leu Gln
        1055                1060                1065

Arg Gln Met Thr Leu Val Pro Pro Ala Tyr Ser Ala Val Thr Thr
        1070                1075                1080

Pro Gly Pro Gly Pro Thr Ser Thr Ser Pro Leu Leu Pro Val Ser
        1085                1090                1095

Pro Leu Pro Thr Leu Thr Leu Asp Ser Leu Ser Gln Val Ser Gln
        1100                1105                1110

Phe Met Ala Cys Glu Glu Leu Pro Pro Gly Ala Pro Glu Leu Pro
        1115                1120                1125

Gln Glu Gly Pro Thr Arg Arg Leu Ser Leu Pro Gly Gln Leu Gly
        1130                1135                1140

Ala Leu Thr Ser Gln Pro Leu His Arg His Gly Ser Asp Pro Gly
        1145                1150                1155

Ser

<210> SEQ ID NO 6
<211> LENGTH: 3480
<212> TYPE: DNA
<213> ORGANISM: homo sapiens

<400> SEQUENCE: 6
atgccggtgc ggaggggcca cgtcgcgccg cagaacacct tcctggacac catcatccgc    60
aagtttgagg ccagagccg taagttcatc atcgccaacg ctcgggtgga gaactgcgcc   120
gtcatctact gcaacgacgg cttctgcgag ctgtgcggct actcgcgggc cgaggtgatg   180
cagcgaccct gcacctgcga cttcctgcac gggccgcgca cgcagcgccg cgctgccgcg   240
cagatcgcgc aggcactgct gggcgccgag gagcgcaaag tggaaatcgc cttctaccgg   300
aaagatggga gctgcttcct atgtctggtg gatgtggtgc ccgtgaagaa cgaggatggg   360
gctgtcatca tgttcatcct caatttcgag gtggtgatgg agaaggacat ggtggggtcc   420
ccggctcatg acaccaacca ccggggcccc cccaccagct ggctggcccc aggccgcgcc   480
aagaccttcc gcctgaagct gcccgcgctg ctggcgctga cggcccggga gtcgtcggtg   540
cggtcgggcg gcgcgggcgg cgcgggcgcc ccggggccg tggtggtgga cgtggacctg   600
acgcccgcgg cacccagcag cgagtcgctg gccctggacg aagtgacagc catggacaac   660
```

```
cacgtggcag ggctcgggcc cgcggaggag cggcgtgcgc tggtgggtcc cggctctccg    720
ccccgcagcg cgcccggcca gctcccatcg ccccgggcgc acagcctcaa ccccgacgcc    780
tcgggctcca gctgcagcct ggcccggacg cgctcccgag aaagctgcgc cagcgtgcgc    840
cgcgcctcgt cggccgacga catcgaggcc atgcgcgccg gggtgctgcc cccgccaccg    900
cgccacgcca gcaccgggc catgcaccca ctgcgcagcg gcttgctcaa ctccacctcg    960
gactccgacc tcgtgcgcta ccgcaccatt agcaagattc cccaaatcac cctcaacttt   1020
gtggacctca agggcgaccc cttcttggct tcgcccacca gtgaccgtga gatcatagca   1080
cctaagataa aggagcgaac ccacaatgtc actgagaagg tcacccaggt cctgtccctg   1140
ggcgccgacg tgctgcctga gtacaagctg caggcaccgc gcatccaccg ctggaccatc   1200
ctgcattaca gccccttcaa ggccgtgtgg gactggctca tcctgctgct ggtcatctac   1260
acggctgtct tcacacccta ctcggctgcc ttcctgctga aggagacgga agaaggcccg   1320
cctgctaccg agtgtggcta cgcctgccag ccgctggctg tggtggacct catcgtggac   1380
atcatgttca ttgtggacat cctcatcaac ttccgcacca cctacgtcaa tgccaacgag   1440
gaggtggtca gccaccccgg ccgcatcgcc gtccactact tcaagggctg gttcctcatc   1500
gacatggtgg ccgccatccc cttcgacctg ctcatcttcg gctctggctc tgaggagctg   1560
atcgggctgc tgaagactgc gcggctgctg cggctggtgc gcgtggcgcg aagctggat   1620
cgctactcag agtacggcgc ggccgtgctg ttcttgctca tgtgcacctt tgcgctcatc   1680
gcgcactggc tagcctgcat ctggtacgcc atcggcaaca tggagcagcc acacatggac   1740
tcacgcatcg gctggctgca aacctgggc gaccagatag gcaaaccta caacagcagc   1800
ggcctgggcg gccctccat caaggacaag tatgtgacgg cgctctactt caccttcagc   1860
agcctcacca gtgtgggctt cggcaacgtc tctcccaaca ccaactcaga aagatcttc   1920
tccatctgcg tcatgctcat tggctccctc atgtatgcta gcatcttcgg caacgtgtcg   1980
gccatcatcc agcggctgta ctcgggcaca gcccgctacc acacacagat gctgcgggtg   2040
cgggagttca tccgcttcca ccagatcccc aatcccctgc gccagcgcct cgaggagtac   2100
ttccagcacg cctggtccta caccaacggc atcgacatga acgcggtgct gaagggcttc   2160
cctgagtgcc tgcaggctga catctgcctg cacctgaacc gctcactgct gcagcactgc   2220
aaacccttcc gagggccac caagggctgc cttcgggccc tggccatgaa gttcaagacc   2280
acacatgcac cgccagggga cacactggtg catgctgggg acctgctcac cgccctgtac   2340
ttcatctccc ggggctccat cgagatcctg cggggcgacg tcgtcgtggc catcctgggg   2400
aagaatgaca tctttgggga gcctctgaac ctgtatgcaa ggcctggcaa gtcgaacggg   2460
gatgtgcggg ccctcaccta ctgtgaccta cacaagatcc atcgggacga cctgctggag   2520
gtgctggaca tgtaccctga gttctccgac cacttctggt ccagcctgga gatcaccttc   2580
aacctgcgag ataccaacat gatcccgggc tcccccggca gtacggagtt agagggtggc   2640
ttcagtcggc aacgcaagcg caagttgtcc ttccgcaggc gcacggacaa ggacacggag   2700
cagccagggg aggtgtcggc cttggggccg gccgggcgg gggcagggcc gagtagccgg   2760
ggccggccgg gggggccgtg gggggagagc ccgtccagtg gcccctccag ccctgagagc   2820
agtgaggatg agggcccagg ccgcagctcc agccccctcc gcctggtgcc cttctccagc   2880
cccaggcccc ccgagagcc gccggtgggg gagcccctga tggaggactg cgagaagagc   2940
agcgacactt gcaaccccct gtcaggcgcc ttctcaggag tgtccaacat tttcagcttc   3000
```

```
tgggggggaca gtcggggccg ccagtaccag gagctccctc gatgcccgc ccccaccccc    3060 agcctcctca acatccccct ctccagcccg ggtcggcggc cccggggcga cgtggagagc    3120
aggctggatg ccctccagcg ccagctcaac aggctggaga cccggctgag tgcagacatg    3180
gccactgtcc tgcagctgct acagaggcag atgacgctgg tcccgcccgc ctacagtgct    3240
gtgaccaccc cggggcctgg ccccacttcc acatccccgc tgttgcccgt cagcccctc    3300 cccaccctca ccttggactc gctttctcag gtttcccagt tcatggcgtg tgaggagctg    3360
cccccggggg ccccagagct tccccaagaa ggccccacac gacgcctctc cctaccgggc    3420
cagctggggg ccctcacctc ccagcccctg cacagacacg gctcggaccc gggcagttag    3480

<210> SEQ ID NO 7
<211> LENGTH: 39
<212> TYPE: DNA
<213> ORGANISM: artificial sequence
<220> FEATURE:
<223> OTHER INFORMATION: primer

<400> SEQUENCE: 7
gactcacgca tcggctggct gcacaaactg ggcgaccag                              39

<210> SEQ ID NO 8
<211> LENGTH: 31
<212> TYPE: DNA
<213> ORGANISM: artificial sequence
<220> FEATURE:
<223> OTHER INFORMATION: primer

<400> SEQUENCE: 8
gtgcagccag ccgatgcgtg agtccatgtg t                                      31

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
ggtctgccca ccctgctctc t                                                 21

<210> SEQ ID NO 10
<211> LENGTH: 22
<212> TYPE: DNA
<213> ORGANISM: artificial sequence
<220> FEATURE:
<223> OTHER INFORMATION: primer

<400> SEQUENCE: 10
cctcttcccc ctctgctcca tt                                                22

<210> SEQ ID NO 11
<211> LENGTH: 21
<212> TYPE: DNA
<213> ORGANISM: artificial sequence
<220> FEATURE:
<223> OTHER INFORMATION: primer

<400> SEQUENCE: 11
agtccaaggg ctctgagcca a                                                 21

<210> SEQ ID NO 12
<211> LENGTH: 25
```

```
<212> TYPE: DNA
<213> ORGANISM: artificial sequence
<220> FEATURE:
<223> OTHER INFORMATION: primer

<400> SEQUENCE: 12
ggtactcagc aggtattaac tgcaa                                            25

<210> SEQ ID NO 13
<211> LENGTH: 23
<212> TYPE: DNA
<213> ORGANISM: artificial sequence
<220> FEATURE:
<223> OTHER INFORMATION: primer

<400> SEQUENCE: 13
ggtagcactg tcctggcagt gat                                              23

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
cctggactca agtcccttc                                                   20

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
tcactccacg taaggaacct g                                                21

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
atgtggactg cagggaggaa gc                                               22

<210> SEQ ID NO 17
<211> LENGTH: 23
<212> TYPE: DNA
<213> ORGANISM: artificial sequence
<220> FEATURE:
<223> OTHER INFORMATION: primer

<400> SEQUENCE: 17
cctttcctcc tctcactgtc tgt                                              23

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
```

```
ggtattctgg tgacaggcac attc                                              24

<210> SEQ ID NO 19
<211> LENGTH: 22
<212> TYPE: DNA
<213> ORGANISM: artificial sequence
<220> FEATURE:
<223> OTHER INFORMATION: primer

<400> SEQUENCE: 19
ccacctctgg ttgcctacac tg                                                22

<210> SEQ ID NO 20
<211> LENGTH: 23
<212> TYPE: DNA
<213> ORGANISM: artificial sequence
<220> FEATURE:
<223> OTHER INFORMATION: primer

<400> SEQUENCE: 20
gtctgcggtc tcacaaagtc ttc                                               23

<210> SEQ ID NO 21
<211> LENGTH: 21
<212> TYPE: DNA
<213> ORGANISM: artificial sequence
<220> FEATURE:
<223> OTHER INFORMATION: primer

<400> SEQUENCE: 21
cgagtgcccc tcaccagcat g                                                 21

<210> SEQ ID NO 22
<211> LENGTH: 22
<212> TYPE: DNA
<213> ORGANISM: artificial sequence
<220> FEATURE:
<223> OTHER INFORMATION: primer

<400> SEQUENCE: 22
ggagactccc ctggcaggac aa                                                22

<210> SEQ ID NO 23
<211> LENGTH: 23
<212> TYPE: DNA
<213> ORGANISM: artificial sequence
<220> FEATURE:
<223> OTHER INFORMATION: primer

<400> SEQUENCE: 23
gggagacaag tccagcccag caa                                               23

<210> SEQ ID NO 24
<211> LENGTH: 22
<212> TYPE: DNA
<213> ORGANISM: artificial sequence
<220> FEATURE:
<223> OTHER INFORMATION: primer

<400> SEQUENCE: 24
agcccacact tgctgtccct tg                                                22

<210> SEQ ID NO 25
<211> LENGTH: 23
<212> TYPE: DNA
<213> ORGANISM: artificial sequence
```

```
<220> FEATURE:
<223> OTHER INFORMATION: primer

<400> SEQUENCE: 25
acttggaaat gccctcaccc aga                                              23

<210> SEQ ID NO 26
<211> LENGTH: 23
<212> TYPE: DNA
<213> ORGANISM: artificial sequence
<220> FEATURE:
<223> OTHER INFORMATION: primer

<400> SEQUENCE: 26
cacctatagg caccatcagt cag                                              23

<210> SEQ ID NO 27
<211> LENGTH: 21
<212> TYPE: DNA
<213> ORGANISM: artificial sequence
<220> FEATURE:
<223> OTHER INFORMATION: primer

<400> SEQUENCE: 27
aaacgtccgt tcctccactc t                                                21

<210> SEQ ID NO 28
<211> LENGTH: 23
<212> TYPE: DNA
<213> ORGANISM: artificial sequence
<220> FEATURE:
<223> OTHER INFORMATION: primer

<400> SEQUENCE: 28
aacccacagc tgggattacc att                                              23

<210> SEQ ID NO 29
<211> LENGTH: 23
<212> TYPE: DNA
<213> ORGANISM: artificial sequence
<220> FEATURE:
<223> OTHER INFORMATION: primer

<400> SEQUENCE: 29
gccagtggct caaaagacag gct                                              23

<210> SEQ ID NO 30
<211> LENGTH: 21
<212> TYPE: DNA
<213> ORGANISM: artificial sequence
<220> FEATURE:
<223> OTHER INFORMATION: primer

<400> SEQUENCE: 30
cctgggcact ggtccggcgc a                                                21

<210> SEQ ID NO 31
<211> LENGTH: 22
<212> TYPE: DNA
<213> ORGANISM: artificial sequence
<220> FEATURE:
<223> OTHER INFORMATION: primer

<400> SEQUENCE: 31
caccacacat cactgctggt gc                                               22
```

```
<210> SEQ ID NO 32
<211> LENGTH: 24
<212> TYPE: DNA
<213> ORGANISM: artificial sequence
<220> FEATURE:
<223> OTHER INFORMATION: primer

<400> SEQUENCE: 32
ggaactgctg atcagtttgg gaga                                              24

<210> SEQ ID NO 33
<211> LENGTH: 23
<212> TYPE: DNA
<213> ORGANISM: artificial sequence
<220> FEATURE:
<223> OTHER INFORMATION: primer

<400> SEQUENCE: 33
cccttttccc cagctgacgc aaa                                               23

<210> SEQ ID NO 34
<211> LENGTH: 24
<212> TYPE: DNA
<213> ORGANISM: artificial sequence
<220> FEATURE:
<223> OTHER INFORMATION: primer

<400> SEQUENCE: 34
gtctaaagca ggccaagaca aatg                                              24

<210> SEQ ID NO 35
<211> LENGTH: 26
<212> TYPE: DNA
<213> ORGANISM: artificial sequence
<220> FEATURE:
<223> OTHER INFORMATION: primer

<400> SEQUENCE: 35
caggaaggta ttccagttac atatga                                            26

<210> SEQ ID NO 36
<211> LENGTH: 23
<212> TYPE: DNA
<213> ORGANISM: artificial sequence
<220> FEATURE:
<223> OTHER INFORMATION: primer

<400> SEQUENCE: 36
acccatgaag ctgtgccagc tgt                                               23

<210> SEQ ID NO 37
<211> LENGTH: 23
<212> TYPE: DNA
<213> ORGANISM: artificial sequence
<220> FEATURE:
<223> OTHER INFORMATION: primer

<400> SEQUENCE: 37
ctttcctatc ccaaacaata cct                                               23

<210> SEQ ID NO 38
<211> LENGTH: 21
<212> TYPE: DNA
<213> ORGANISM: artificial sequence
<220> FEATURE:
<223> OTHER INFORMATION: primer
```

```
<400> SEQUENCE: 38
ccccaccatc ccccatgcag t                                         21

<210> SEQ ID NO 39
<211> LENGTH: 27
<212> TYPE: DNA
<213> ORGANISM: artificial sequence
<220> FEATURE:
<223> OTHER INFORMATION: primer

<400> SEQUENCE: 39
gagccagaga ccttcacaag gtcccct                                   27

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
cccttgccac ttaccacaag                                           20

<210> SEQ ID NO 41
<211> LENGTH: 23
<212> TYPE: DNA
<213> ORGANISM: artificial sequence
<220> FEATURE:
<223> OTHER INFORMATION: primer

<400> SEQUENCE: 41
gggactggat ggcttggcat ggt                                       23

<210> SEQ ID NO 42
<211> LENGTH: 22
<212> TYPE: DNA
<213> ORGANISM: artificial sequence
<220> FEATURE:
<223> OTHER INFORMATION: primer

<400> SEQUENCE: 42
cggggagtag ggggtggcaa tg                                        22

<210> SEQ ID NO 43
<211> LENGTH: 22
<212> TYPE: DNA
<213> ORGANISM: artificial sequence
<220> FEATURE:
<223> OTHER INFORMATION: primer

<400> SEQUENCE: 43
gcccagggcc agctgcccag ct                                        22

<210> SEQ ID NO 44
<211> LENGTH: 26
<212> TYPE: DNA
<213> ORGANISM: artificial sequence
<220> FEATURE:
<223> OTHER INFORMATION: primer

<400> SEQUENCE: 44
ctgtatatgt aggtgcctta tacatg                                    26

<210> SEQ ID NO 45
```

```
<211> LENGTH: 22
<212> TYPE: DNA
<213> ORGANISM: artificial sequence
<220> FEATURE:
<223> OTHER INFORMATION: primer

<400> SEQUENCE: 45
agggtctaaa cccccagggt ca                                              22

<210> SEQ ID NO 46
<211> LENGTH: 22
<212> TYPE: DNA
<213> ORGANISM: artificial sequence
<220> FEATURE:
<223> OTHER INFORMATION: primer

<400> SEQUENCE: 46
cccagctggc ttcagggaca aa                                              22

<210> SEQ ID NO 47
<211> LENGTH: 22
<212> TYPE: DNA
<213> ORGANISM: artificial sequence
<220> FEATURE:
<223> OTHER INFORMATION: primer

<400> SEQUENCE: 47
gaggccaaag gctgctactc ag                                              22

<210> SEQ ID NO 48
<211> LENGTH: 22
<212> TYPE: DNA
<213> ORGANISM: artificial sequence
<220> FEATURE:
<223> OTHER INFORMATION: primer

<400> SEQUENCE: 48
cctgtcccct ctgggtggaa ct                                              22

<210> SEQ ID NO 49
<211> LENGTH: 22
<212> TYPE: DNA
<213> ORGANISM: artificial sequence
<220> FEATURE:
<223> OTHER INFORMATION: primer

<400> SEQUENCE: 49
acaggccctg aggtgggcct ga                                              22

<210> SEQ ID NO 50
<211> LENGTH: 23
<212> TYPE: DNA
<213> ORGANISM: artificial sequence
<220> FEATURE:
<223> OTHER INFORMATION: primer

<400> SEQUENCE: 50
tgacctgact ttccagctgg aga                                             23

<210> SEQ ID NO 51
<211> LENGTH: 24
<212> TYPE: DNA
<213> ORGANISM: artificial sequence
<220> FEATURE:
<223> OTHER INFORMATION: primer

<400> SEQUENCE: 51
```

-continued

```
tccaggcttc atgtccacct gtct                                          24

<210> SEQ ID NO 52
<211> LENGTH: 21
<212> TYPE: DNA
<213> ORGANISM: artificial sequence
<220> FEATURE:
<223> OTHER INFORMATION: primer

<400> SEQUENCE: 52
tctcccgcac cggcaatggg t                                             21

<210> SEQ ID NO 53
<211> LENGTH: 22
<212> TYPE: DNA
<213> ORGANISM: artificial sequence
<220> FEATURE:
<223> OTHER INFORMATION: primer

<400> SEQUENCE: 53
agtggggagc tgttcccatc ct                                            22

<210> SEQ ID NO 54
<211> LENGTH: 17
<212> TYPE: DNA
<213> ORGANISM: artificial sequence
<220> FEATURE:
<223> OTHER INFORMATION: primer

<400> SEQUENCE: 54
ggaccgcctc ccactcc                                                  17

<210> SEQ ID NO 55
<211> LENGTH: 23
<212> TYPE: DNA
<213> ORGANISM: artificial sequence
<220> FEATURE:
<223> OTHER INFORMATION: primer

<400> SEQUENCE: 55
ttgaaaagga aatgtgctct ggg                                           23

<210> SEQ ID NO 56
<211> LENGTH: 21
<212> TYPE: DNA
<213> ORGANISM: artificial sequence
<220> FEATURE:
<223> OTHER INFORMATION: primer

<400> SEQUENCE: 56
aacatcatgg gtgatggcca t                                             21

<210> SEQ ID NO 57
<211> LENGTH: 26
<212> TYPE: DNA
<213> ORGANISM: artificial sequence
<220> FEATURE:
<223> OTHER INFORMATION: primer

<400> SEQUENCE: 57
ctcaagcgag gtacagaatt aaatga                                        26

<210> SEQ ID NO 58
<211> LENGTH: 24
<212> TYPE: DNA
```

<210> SEQ ID NO 59
<211> LENGTH: 23
<212> TYPE: DNA
<213> ORGANISM: artificial sequence
<220> FEATURE:
<223> OTHER INFORMATION: primer

<400> SEQUENCE: 58
gggctttcag atgcagacac tgat                                    24

<210> SEQ ID NO 59
<211> LENGTH: 23
<212> TYPE: DNA
<213> ORGANISM: artificial sequence
<220> FEATURE:
<223> OTHER INFORMATION: primer

<400> SEQUENCE: 59
gcctgtctga tctccctgtg tga                                     23

<210> SEQ ID NO 60
<211> LENGTH: 22
<212> TYPE: DNA
<213> ORGANISM: artificial sequence
<220> FEATURE:
<223> OTHER INFORMATION: primer

<400> SEQUENCE: 60
cctgtctggt ctccctgtgt ca                                      22

<210> SEQ ID NO 61
<211> LENGTH: 22
<212> TYPE: DNA
<213> ORGANISM: artificial sequence
<220> FEATURE:
<223> OTHER INFORMATION: primer

<400> SEQUENCE: 61
ccatgctggg gcctctgaga ac                                      22

<210> SEQ ID NO 62
<211> LENGTH: 22
<212> TYPE: DNA
<213> ORGANISM: artificial sequence
<220> FEATURE:
<223> OTHER INFORMATION: primer

<400> SEQUENCE: 62
ggctctgatg gctggccatg tg                                      22

<210> SEQ ID NO 63
<211> LENGTH: 22
<212> TYPE: DNA
<213> ORGANISM: artificial sequence
<220> FEATURE:
<223> OTHER INFORMATION: primer

<400> SEQUENCE: 63
cccagcgagc actttccatt tg                                      22

<210> SEQ ID NO 64
<211> LENGTH: 24
<212> TYPE: DNA
<213> ORGANISM: artificial sequence
<220> FEATURE:
<223> OTHER INFORMATION: primer

<400> SEQUENCE: 64
gcttctccgt ccagctgact tgta                                    24

<210> SEQ ID NO 65
<211> LENGTH: 22
<212> TYPE: DNA
<213> ORGANISM: artificial sequence
<220> FEATURE:
<223> OTHER INFORMATION: primer

<400> SEQUENCE: 65
tgcacagtga tgctggctgg aa                                              22

<210> SEQ ID NO 66
<211> LENGTH: 23
<212> TYPE: DNA
<213> ORGANISM: artificial sequence
<220> FEATURE:
<223> OTHER INFORMATION: primer

<400> SEQUENCE: 66
gaagaggcac agcatgctgt tgg                                             23

<210> SEQ ID NO 67
<211> LENGTH: 21
<212> TYPE: DNA
<213> ORGANISM: artificial sequence
<220> FEATURE:
<223> OTHER INFORMATION: primer

<400> SEQUENCE: 67
aagtgggagg ctggcatcga c                                               21

<210> SEQ ID NO 68
<211> LENGTH: 21
<212> TYPE: DNA
<213> ORGANISM: artificial sequence
<220> FEATURE:
<223> OTHER INFORMATION: primer

<400> SEQUENCE: 68
gtccccactc accatgggca g                                               21

<210> SEQ ID NO 69
<211> LENGTH: 21
<212> TYPE: DNA
<213> ORGANISM: artificial sequence
<220> FEATURE:
<223> OTHER INFORMATION: primer

<400> SEQUENCE: 69
gtcctgtctg actttgccga c                                               21

<210> SEQ ID NO 70
<211> LENGTH: 22
<212> TYPE: DNA
<213> ORGANISM: artificial sequence
<220> FEATURE:
<223> OTHER INFORMATION: primer

<400> SEQUENCE: 70
catttcttac tcccaaagcc ag                                              22

<210> SEQ ID NO 71
<211> LENGTH: 22
<212> TYPE: DNA
<213> ORGANISM: artificial sequence
<220> FEATURE:

<223> OTHER INFORMATION: primer

<400> SEQUENCE: 71
cttgagtgtg gaggagataa gc                                              22

<210> SEQ ID NO 72
<211> LENGTH: 22
<212> TYPE: DNA
<213> ORGANISM: artificial sequence
<220> FEATURE:
<223> OTHER INFORMATION: primer

<400> SEQUENCE: 72
caaattcccg agagccagaa ac                                              22

<210> SEQ ID NO 73
<211> LENGTH: 19
<212> TYPE: DNA
<213> ORGANISM: artificial sequence
<220> FEATURE:
<223> OTHER INFORMATION: primer

<400> SEQUENCE: 73
caggtgcatc tgtgggatg                                                  19

<210> SEQ ID NO 74
<211> LENGTH: 19
<212> TYPE: DNA
<213> ORGANISM: artificial sequence
<220> FEATURE:
<223> OTHER INFORMATION: primer

<400> SEQUENCE: 74
ggaccaatgt gtgggcaag                                                  19

<210> SEQ ID NO 75
<211> LENGTH: 21
<212> TYPE: DNA
<213> ORGANISM: artificial sequence
<220> FEATURE:
<223> OTHER INFORMATION: primer

<400> SEQUENCE: 75
gttcaaacag gttgcagggt c                                               21

<210> SEQ ID NO 76
<211> LENGTH: 22
<212> TYPE: DNA
<213> ORGANISM: artificial sequence
<220> FEATURE:
<223> OTHER INFORMATION: primer

<400> SEQUENCE: 76
cttaggggac tccatctggt ag                                              22

<210> SEQ ID NO 77
<211> LENGTH: 19
<212> TYPE: DNA
<213> ORGANISM: artificial sequence
<220> FEATURE:
<223> OTHER INFORMATION: primer

<400> SEQUENCE: 77
gtgtatgctc ttccctggg                                                  19

```
<210> SEQ ID NO 78
<211> LENGTH: 20
<212> TYPE: DNA
<213> ORGANISM: artificial sequence
<220> FEATURE:
<223> OTHER INFORMATION: primer

<400> SEQUENCE: 78
gcatctgagc aaggtggatg                                                   20

<210> SEQ ID NO 79
<211> LENGTH: 19
<212> TYPE: DNA
<213> ORGANISM: artificial sequence
<220> FEATURE:
<223> OTHER INFORMATION: primer

<400> SEQUENCE: 79
cgtgaacagc tgagcccag                                                    19

<210> SEQ ID NO 80
<211> LENGTH: 22
<212> TYPE: DNA
<213> ORGANISM: artificial sequence
<220> FEATURE:
<223> OTHER INFORMATION: primer

<400> SEQUENCE: 80
catctcaagc tgtcctagtg tg                                                22

<210> SEQ ID NO 81
<211> LENGTH: 18
<212> TYPE: DNA
<213> ORGANISM: artificial sequence
<220> FEATURE:
<223> OTHER INFORMATION: primer

<400> SEQUENCE: 81
gactcgctgc cttaggcg                                                     18

<210> SEQ ID NO 82
<211> LENGTH: 20
<212> TYPE: DNA
<213> ORGANISM: artificial sequence
<220> FEATURE:
<223> OTHER INFORMATION: primer

<400> SEQUENCE: 82
gaagtctcaa gacaccagtg                                                   20

<210> SEQ ID NO 83
<211> LENGTH: 19
<212> TYPE: DNA
<213> ORGANISM: artificial sequence
<220> FEATURE:
<223> OTHER INFORMATION: primer

<400> SEQUENCE: 83
catcagagtg gtgggtttg                                                    19

<210> SEQ ID NO 84
<211> LENGTH: 19
<212> TYPE: DNA
<213> ORGANISM: artificial sequence
<220> FEATURE:
<223> OTHER INFORMATION: primer
```

<400> SEQUENCE: 84
ctgaacgtaa gtgggtctg                                            19

<210> SEQ ID NO 85
<211> LENGTH: 20
<212> TYPE: DNA
<213> ORGANISM: artificial sequence
<220> FEATURE:
<223> OTHER INFORMATION: primer

<400> SEQUENCE: 85
caacggtgac cggtaaccac                                           20

<210> SEQ ID NO 86
<211> LENGTH: 23
<212> TYPE: DNA
<213> ORGANISM: artificial sequence
<220> FEATURE:
<223> OTHER INFORMATION: primer

<400> SEQUENCE: 86
ctggatgcaa caataacagt gac                                       23

<210> SEQ ID NO 87
<211> LENGTH: 20
<212> TYPE: DNA
<213> ORGANISM: artificial sequence
<220> FEATURE:
<223> OTHER INFORMATION: primer

<400> SEQUENCE: 87
gagctgtagc ttccataagg                                           20

<210> SEQ ID NO 88
<211> LENGTH: 21
<212> TYPE: DNA
<213> ORGANISM: artificial sequence
<220> FEATURE:
<223> OTHER INFORMATION: primer

<400> SEQUENCE: 88
ctgtaccaag ccaaatgcat g                                         21

<210> SEQ ID NO 89
<211> LENGTH: 19
<212> TYPE: DNA
<213> ORGANISM: artificial sequence
<220> FEATURE:
<223> OTHER INFORMATION: primer

<400> SEQUENCE: 89
ctgtccgggt gtatgtggc                                            19

<210> SEQ ID NO 90
<211> LENGTH: 20
<212> TYPE: DNA
<213> ORGANISM: artificial sequence
<220> FEATURE:
<223> OTHER INFORMATION: primer

<400> SEQUENCE: 90
caaaaaaggc agtgaccttc                                           20

<210> SEQ ID NO 91
<211> LENGTH: 18

```
<212> TYPE: DNA
<213> ORGANISM: artificial sequence
<220> FEATURE:
<223> OTHER INFORMATION: primer

<400> SEQUENCE: 91
cacagcactg gcaggttg                                                18

<210> SEQ ID NO 92
<211> LENGTH: 19
<212> TYPE: DNA
<213> ORGANISM: artificial sequence
<220> FEATURE:
<223> OTHER INFORMATION: primer

<400> SEQUENCE: 92
ggccagagag caaggcttc                                               19

<210> SEQ ID NO 93
<211> LENGTH: 19
<212> TYPE: DNA
<213> ORGANISM: artificial sequence
<220> FEATURE:
<223> OTHER INFORMATION: primer

<400> SEQUENCE: 93
cagtctgcgt gctcctcag                                               19

<210> SEQ ID NO 94
<211> LENGTH: 20
<212> TYPE: DNA
<213> ORGANISM: artificial sequencej
<220> FEATURE:
<223> OTHER INFORMATION: primer

<400> SEQUENCE: 94
ccttgacacc ctccactatg                                              20

<210> SEQ ID NO 95
<211> LENGTH: 19
<212> TYPE: DNA
<213> ORGANISM: artificial sequence
<220> FEATURE:
<223> OTHER INFORMATION: primer

<400> SEQUENCE: 95
caggtcttca caagcctcc                                               19

<210> SEQ ID NO 96
<211> LENGTH: 20
<212> TYPE: DNA
<213> ORGANISM: artificial sequence
<220> FEATURE:
<223> OTHER INFORMATION: primer

<400> SEQUENCE: 96
gttgagaggc aagaactcag                                              20

<210> SEQ ID NO 97
<211> LENGTH: 19
<212> TYPE: DNA
<213> ORGANISM: artificial sequence
<220> FEATURE:
<223> OTHER INFORMATION: primer

<400> SEQUENCE: 97
```

| | |
|---|---|
| caagctgtct gtcccacag | 19 |

<210> SEQ ID NO 98
<211> LENGTH: 22
<212> TYPE: DNA
<213> ORGANISM: artificial sequence
<220> FEATURE:
<223> OTHER INFORMATION: primer

<400> SEQUENCE: 98

| | |
|---|---|
| ctggctttca tttcatgtca tg | 22 |

<210> SEQ ID NO 99
<211> LENGTH: 22
<212> TYPE: DNA
<213> ORGANISM: artificial sequence
<220> FEATURE:
<223> OTHER INFORMATION: primer

<400> SEQUENCE: 99

| | |
|---|---|
| gtaggtttag gcattttgac tc | 22 |

<210> SEQ ID NO 100
<211> LENGTH: 20
<212> TYPE: DNA
<213> ORGANISM: artificial sequence
<220> FEATURE:
<223> OTHER INFORMATION: primer

<400> SEQUENCE: 100

| | |
|---|---|
| cttcacgttc acacgcagac | 20 |

<210> SEQ ID NO 101
<211> LENGTH: 18
<212> TYPE: DNA
<213> ORGANISM: artificial sequence
<220> FEATURE:
<223> OTHER INFORMATION: primer

<400> SEQUENCE: 101

| | |
|---|---|
| ctgaggctgt ctgcacac | 18 |

<210> SEQ ID NO 102
<211> LENGTH: 18
<212> TYPE: DNA
<213> ORGANISM: artificial sequence
<220> FEATURE:
<223> OTHER INFORMATION: primer

<400> SEQUENCE: 102

| | |
|---|---|
| gtggcctcct tcagagag | 18 |

<210> SEQ ID NO 103
<211> LENGTH: 18
<212> TYPE: DNA
<213> ORGANISM: artificial sequence
<220> FEATURE:
<223> OTHER INFORMATION: primer

<400> SEQUENCE: 103

| | |
|---|---|
| ggcagacagg tgtgccgg | 18 |

<210> SEQ ID NO 104
<211> LENGTH: 19
<212> TYPE: DNA
<213> ORGANISM: artificial sequence

```
<220> FEATURE:
<223> OTHER INFORMATION: primer

<400> SEQUENCE: 104
ccatccacac tcggaagag                                                    19

<210> SEQ ID NO 105
<211> LENGTH: 20
<212> TYPE: DNA
<213> ORGANISM: artificial sequence
<220> FEATURE:
<223> OTHER INFORMATION: primer

<400> SEQUENCE: 105
ctgtgtgagt ggagaatgtg                                                   20

<210> SEQ ID NO 106
<211> LENGTH: 20
<212> TYPE: DNA
<213> ORGANISM: artificial sequence
<220> FEATURE:
<223> OTHER INFORMATION: primer

<400> SEQUENCE: 106
gtggtcccgc ccctcttgac                                                   20

<210> SEQ ID NO 107
<211> LENGTH: 20
<212> TYPE: DNA
<213> ORGANISM: artificial sequence
<220> FEATURE:
<223> OTHER INFORMATION: primer

<400> SEQUENCE: 107
cttgggttcc agggtccatc                                                   20

<210> SEQ ID NO 108
<211> LENGTH: 19
<212> TYPE: DNA
<213> ORGANISM: artificial sequence
<220> FEATURE:
<223> OTHER INFORMATION: primer

<400> SEQUENCE: 108
gaccttggac agctcacag                                                    19

<210> SEQ ID NO 109
<211> LENGTH: 19
<212> TYPE: DNA
<213> ORGANISM: artificial sequence
<220> FEATURE:
<223> OTHER INFORMATION: primer

<400> SEQUENCE: 109
gtccatttcc caggccttg                                                    19

<210> SEQ ID NO 110
<211> LENGTH: 22
<212> TYPE: DNA
<213> ORGANISM: artificial sequence
<220> FEATURE:
<223> OTHER INFORMATION: primer

<400> SEQUENCE: 110
gacgtagtga aaaggtcaga ag                                                22
```

```
<210> SEQ ID NO 111
<211> LENGTH: 20
<212> TYPE: DNA
<213> ORGANISM: artificial sequence
<220> FEATURE:
<223> OTHER INFORMATION: primer

<400> SEQUENCE: 111
gtctccactc tcgatctatg                                                     20

<210> SEQ ID NO 112
<211> LENGTH: 18
<212> TYPE: DNA
<213> ORGANISM: artificial sequence
<220> FEATURE:
<223> OTHER INFORMATION: primer

<400> SEQUENCE: 112
cccggctctg gatcacag                                                       18

<210> SEQ ID NO 113
<211> LENGTH: 20
<212> TYPE: DNA
<213> ORGANISM: artificial sequence
<220> FEATURE:
<223> OTHER INFORMATION: primer

<400> SEQUENCE: 113
cagagatgtc atcgctcctg                                                     20

<210> SEQ ID NO 114
<211> LENGTH: 20
<212> TYPE: DNA
<213> ORGANISM: artificial sequence
<220> FEATURE:
<223> OTHER INFORMATION: primer

<400> SEQUENCE: 114
cactacctcc caccacattc                                                     20

<210> SEQ ID NO 115
<211> LENGTH: 20
<212> TYPE: DNA
<213> ORGANISM: artificial sequence
<220> FEATURE:
<223> OTHER INFORMATION: primer

<400> SEQUENCE: 115
cttgccccat caacggaatg                                                     20

<210> SEQ ID NO 116
<211> LENGTH: 20
<212> TYPE: DNA
<213> ORGANISM: artificial sequence
<220> FEATURE:
<223> OTHER INFORMATION: primer

<400> SEQUENCE: 116
ctagcagcct cagtttcctc                                                     20

<210> SEQ ID NO 117
<211> LENGTH: 19
<212> TYPE: DNA
<213> ORGANISM: artificial sequence
<220> FEATURE:
<223> OTHER INFORMATION: primer
```

<400> SEQUENCE: 117
ctgagactga gacactgac                                              19

<210> SEQ ID NO 118
<211> LENGTH: 21
<212> TYPE: DNA
<213> ORGANISM: artificial sequence
<220> FEATURE:
<223> OTHER INFORMATION: primer

<400> SEQUENCE: 118
gtccttacta ctgactgtga c                                           21

<210> SEQ ID NO 119
<211> LENGTH: 21
<212> TYPE: DNA
<213> ORGANISM: artificial sequence
<220> FEATURE:
<223> OTHER INFORMATION: primer

<400> SEQUENCE: 119
ctggaggttg agatttctct g                                           21

<210> SEQ ID NO 120
<211> LENGTH: 20
<212> TYPE: DNA
<213> ORGANISM: artificial sequence
<220> FEATURE:
<223> OTHER INFORMATION: primer

<400> SEQUENCE: 120
gaaggctcgc acctcttgag                                             20

<210> SEQ ID NO 121
<211> LENGTH: 18
<212> TYPE: DNA
<213> ORGANISM: artificial sequence
<220> FEATURE:
<223> OTHER INFORMATION: primer

<400> SEQUENCE: 121
gtgcctgctg cctggatg                                               18

<210> SEQ ID NO 122
<211> LENGTH: 22
<212> TYPE: DNA
<213> ORGANISM: artificial sequence
<220> FEATURE:
<223> OTHER INFORMATION: primer

<400> SEQUENCE: 122
cattcaatgt cacacagcaa ag                                          22

<210> SEQ ID NO 123
<211> LENGTH: 21
<212> TYPE: DNA
<213> ORGANISM: artificial sequence
<220> FEATURE:
<223> OTHER INFORMATION: primer

<400> SEQUENCE: 123
ctgtgttaag gagggagctt g                                           21

<210> SEQ ID NO 124

```
<211> LENGTH: 19
<212> TYPE: DNA
<213> ORGANISM: artificial sequence
<220> FEATURE:
<223> OTHER INFORMATION: primer

<400> SEQUENCE: 124
gcctgggtaa agcagacac                                               19

<210> SEQ ID NO 125
<211> LENGTH: 19
<212> TYPE: DNA
<213> ORGANISM: artificial sequence
<220> FEATURE:
<223> OTHER INFORMATION: primer

<400> SEQUENCE: 125
ctcctctctg ttctcctcc                                               19

<210> SEQ ID NO 126
<211> LENGTH: 19
<212> TYPE: DNA
<213> ORGANISM: artificial sequence
<220> FEATURE:
<223> OTHER INFORMATION: primer

<400> SEQUENCE: 126
cagagagcag agctgggtg                                               19

<210> SEQ ID NO 127
<211> LENGTH: 18
<212> TYPE: DNA
<213> ORGANISM: artificial sequence
<220> FEATURE:
<223> OTHER INFORMATION: primer

<400> SEQUENCE: 127
ctgtcaggta tcccgggc                                                18

<210> SEQ ID NO 128
<211> LENGTH: 19
<212> TYPE: DNA
<213> ORGANISM: artificial sequence
<220> FEATURE:
<223> OTHER INFORMATION: primer

<400> SEQUENCE: 128
caggacctgg accagactc                                               19

<210> SEQ ID NO 129
<211> LENGTH: 19
<212> TYPE: DNA
<213> ORGANISM: artificial sequence
<220> FEATURE:
<223> OTHER INFORMATION: primer

<400> SEQUENCE: 129
gtggaggctg tcactggtg                                               19

<210> SEQ ID NO 130
<211> LENGTH: 22
<212> TYPE: DNA
<213> ORGANISM: artificial sequence
<220> FEATURE:
<223> OTHER INFORMATION: primer

<400> SEQUENCE: 130
```

```
gaaaggcagc aaagcaggtt tg                                              22

<210> SEQ ID NO 131
<211> LENGTH: 19
<212> TYPE: DNA
<213> ORGANISM: artificial sequence
<220> FEATURE:
<223> OTHER INFORMATION: primer

<400> SEQUENCE: 131
gttctcctgc cccttccc                                                   19

<210> SEQ ID NO 132
<211> LENGTH: 19
<212> TYPE: DNA
<213> ORGANISM: artificial sequence
<220> FEATURE:
<223> OTHER INFORMATION: primer

<400> SEQUENCE: 132
ctttcgagtt cctctcccc                                                  19

<210> SEQ ID NO 133
<211> LENGTH: 19
<212> TYPE: DNA
<213> ORGANISM: artificial sequence
<220> FEATURE:
<223> OTHER INFORMATION: primer

<400> SEQUENCE: 133
cagtgtggac acgtggctc                                                  19

<210> SEQ ID NO 134
<211> LENGTH: 22
<212> TYPE: DNA
<213> ORGANISM: artificial sequence
<220> FEATURE:
<223> OTHER INFORMATION: primer

<400> SEQUENCE: 134
ctatgcatgt ccagacagga ac                                              22
```

MUTATIONS IN ION CHANNEL PROTEINS ASSOCIATED WITH SUDDEN CARDIAC DEATH

CROSS-REFERENCE TO RELATED APPLICATION

This application is a divisional of U.S. patent application Ser. No. 10/924,375 filed Aug. 23, 2004, now allowed, which claims the benefit of and priority to U.S. Provisional Application No. 60/497,256, filed Aug. 22, 2003, the entire contents of each of which are hereby incorporated by reference.

BACKGROUND

1. Technical Field

The invention relates to diagnosis of sudden cardiac death or potential for sudden cardiac death in patients who have mutations in ion channels proteins involved in electrophysiology of the heart.

2. Background of Related Art

Sudden cardiac death takes the lives of over 300,000 Americans annually. Malignant ventricular arrhythmias occurring in individuals with structurally normal hearts account for a subgroup of these sudden deaths. This form of cardiac disease accounts for approximately 20% of sudden cardiac death cases. Recent years have witnessed major strides in the understanding of sudden cardiac death in individuals with structurally normal heart. Idiopathic, sudden cardiac death syndromes for which there was previously no explanation are gradually coming into focus as forms of inherited ion channelopathies.

The QT interval is the surrogate electrocardiographic index of ventricular repolarization and its duration under normal conditions is mainly determined by expression, properties, and balance of the repolarising inward sodium and calcium and outward potassium and chloride currents. Ion channels proteins are responsible for the currents that comprise the cardiac action potential and alterations in ion channel function are known to be associated with a wide spectrum of phenotypes. Long QT syndrome (LQT) is characterized by the appearance of a long QT interval in the electrocardiogram, and an atypical polymorphic ventricular tachycardia known as torsades de pointes, and a high risk of sudden cardiac death. Congenital LQT syndrome is an inherited condition of abnormal cardiac repolarization. Acquired LQT syndrome is similar to congenital LQT syndrome but can be caused by exposure to drugs, trauma or other environmental factors. Gain of function in SCN5A, the gene that encodes for the α subunit of the cardiac sodium channel, is associated with the LQT3 form of the Long QT syndrome (See, e.g., U.S. Pat. No. 5,599,673), while a decrease in function of the same channel is associated with Brugada syndrome and familial conduction disease. Likewise, loss of function in $I_{Ks}$ and $I_{Kr}$ is linked to other forms of Long QT, while an increase in $I_{Ks}$ current, caused by a mutation in the α subunit KCNQ1 (also referred to as KvLQT1), is linked to familial atrial fibrillation. The final common pathway is similar, involving alteration of ion channel activity, leading to the development of an arrhythmogenic substrate.

U.S. Pat. Nos. 6,582,913, 6,451,534, 6,432,644 and 6,277,978 are directed to screening and/or diagnosis of Long QT syndrome by analyzing the DNA sequence of the KvLQT1 or KCNE1 genes and molecular variants of these genes which cause or are involved in the pathogenesis of Long QT syndrome. U.S. Pat. Nos. 6,420,124 and 6,274,332 are directed to screening for drugs useful in treating a person having certain mutations in the KvLQT1 or KCNE1 genes. U.S. Pat. No. 6,458,542 is directed to a method for screening for susceptibility to drug induced cardiac arrhythmia by detecting a polymorphism in the KCNE1 gene. Certain mutations in the HERG (also known as KCNH2) gene have also been linked to LQT syndrome. See, e.g., U.S. Pat. No. 6,207,383.

Brugada syndrome is associated with sudden cardiac death and ventricular arrhythmia and may occur in the structurally normal heart. It is characterized by ST segment elevation in the right precordial leads (V1 to V3) and right bundle branch block. The age of onset of clinical manifestations, which can include syncope or cardiac arrest, is typically in the third or fourth decade of life. Cardiac events may occur during sleep or at rest. A loss of ion channel function in Brugada syndrome has been associated with certain mutations of the SCN5A protein.

Progressive cardiac conduction defect, also known as progressive conduction disease or Lenegre disease is another electrophysiological cardiac syndrome that is considered one of the most common. It is characterized by a progressive alteration of cardiac conduction through the atrioventricular node, His-Purkinje system with left or right bundle block, which may cause syncope or sudden death. Scott et al., Nat. Genet., (1998) 23:20-21, indicate that certain mutations in SCN5A are associated with progressive conduction disease.

Short QT syndrome (SQT) is a new clinical entity originally described in 2000. Short QT syndrome is characterized by the presence of a very short QT interval in the electrocardiogram (Bazzett-corrected QT interval (QTc) of ≦300 msec), episodes of paroxysmal atrial fibrillation, ventricular arrhythmias and possible sudden death in patients with structurally normal hearts. An autosomal dominant pattern of transmission with a high incidence of sudden death over several generations has been reported.

There is a need to determine the underlying cause of sudden cardiac death so that diagnostic procedures can be implemented to take precautions in susceptible individuals and to aid in determinations of mortality risk.

SUMMARY

In one aspect, the genetic basis for a new clinical entity, characterized by sudden death and short QT intervals in the electrocardiogram is identified. Two different missense mutations are associated with the same amino acid change (N588K) in the S5-P loop region of the cardiac $I_{Kr}$ channel HERG (KCNH2). The mutations dramatically increase $I_{Kr}$, leading to heterogeneous abbreviation of action potential duration and refractoriness.

In another aspect, previously unknown mutations in the SCN5A gene are associated with Brugada syndrome. Mutations at the following positions in the protein encoded by SCN5A (also known as $Na_v1.5$) are identified herein as R104W, R179 stop, T220I, G400A, E446K, F532C, A735V, R878C, H886P, L917R, E1573K, C1727R, V232I+L1307F, P336L+I1659V, Y1614 stop, deletion from E1573-G1604, and insertion of TG at 851.

In another aspect, a previously unknown mutation in the KCNQ1 protein is associated with Long QT syndrome, namely, G189W. In another aspect, previously unknown mutations of the protein encoded by the KCNH2 gene, namely, R356H, a C deletion at 764, and a W398 stop are associated with Long QT syndrome. In another aspect, a previously unknown mutation of the protein encoded by SCN5A ($Na_v1.5$), namely, S1134I, is associated with Long QT syndrome.

In another aspect, a previously unknown mutation of the protein encoded by SCN5A (Na$_v$1.5), namely, P1008S, is associated with progressive conduction disease.

In accordance with the present invention, the above-identified mutations are utilized to diagnose and screen for sudden cardiac death or to determine susceptibility to cardiac death. Nucleic acid probes are provided which selectively hybridize to the mutant nucleic acids described herein. Antibodies are provided which selectively bind to the mutant proteins described herein. The above-identified mutations are also utilized to screen for drugs useful in treating the symptoms manifest by such mutations.

DETAILED DESCRIPTION OF PREFERRED EMBODIMENTS

Figure 1:
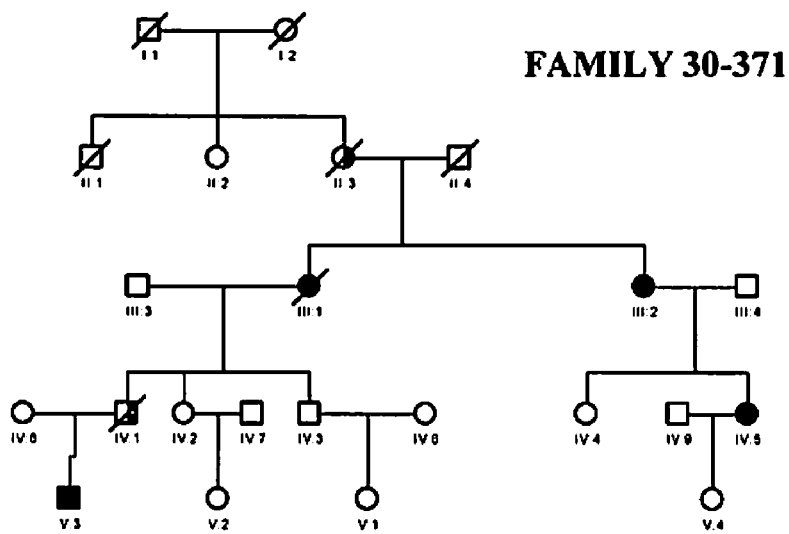
FIG. 1 illustrates the pedigree of families 30-371 and 30-335 with familial Short QT syndrome. Filled circles and squares indicate affected individuals with abnormal QT interval. Half-filled circles and squares indicate individuals who suffered sudden cardiac death. Crossed circles and squares indicate deceased individuals.
Figure 1:
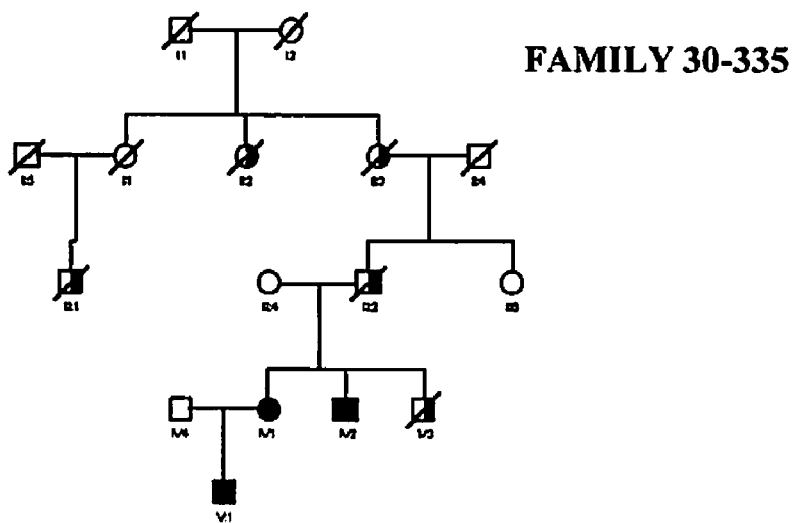

In accordance with the present invention, previously unknown mutations of genes and their corresponding proteins are disclosed which are involved with ion channels associated with arrhythmias and/or sudden cardiac death.

In one aspect, the invention relates to the identification of a molecular basis of short QT syndrome. More specifically, a missense mutation in the KCNH2 gene (Seq. Id. No. 6) (also referred to as the HERG gene) causes a N588K mutation of the KCNH2 protein (Seq. Id. No. 5) and short QT syndrome. Although arrhythmic diseases have been linked to gain of function, e.g., in SCN5A (late I$_{Na}$) and KCNQ1 (I$_{Ks}$), no disease had previously been associated with a gain of function in KCNH2 encoding for I$_{Kr}$. The N588K mutation dramatically increases I$_{Kr}$, leading to heterogeneous abbreviation of action potential duration and refractoriness, and a reduction of the affinity of the channel to I$_{Kr}$ blockers. A novel genetic and biophysical mechanism is described herein which may be responsible for Sudden Infant Death Syndrome (SIDS), sudden death in children and in young adults caused by mutations in KCNH2. KCNH2 is the binding target for several cardiac and non-cardiac pharmacologic compounds.

In another aspect, previously unknown mutations in the SCN5A gene (Seq. Id. No. 4) are associated with Brugada syndrome. Mutations at one or more of the following positions in the protein encoded by the SCN5A gene (Na$_v$1.5) (Seq. Id. No. 3) are identified herein as R104W, R179 stop, T220I, G400A, E446K, F532C, A735V, R878C, H886P, L917R, E1573K, C1727R, V232I+L1307F, P336L+I1659V, Y1614 stop codon, deletion from E1573-G1604, and insertion of TG at 851.

In another aspect, a previously unknown mutation in the KCNQ1 protein (Seq. Id. No. 1), G189W is associated with Long QT syndrome. In another aspect, previously unknown mutations of the protein encoded by KCNH2 nucleic acid, namely, at least one of R356H, a C deletion at 764, and a W398 stop, are associated with Long QT syndrome. In another aspect, a previously unknown mutation of the protein encoded by SCN5A (Na$_v$1.5), namely, S1134I, is associated with Long QT syndrome.

In another aspect, a previously unknown mutation of the protein encoded by SCN5A (Na$_v$1.5), namely, P1008S, is associated with progressive conduction disease.

Analysis of these genes provides an early diagnosis of subjects with short QT syndrome (mutated KCNH2 as described above), Brugada syndrome (mutated SCN5A as described above), Long QT syndrome (mutated KCNQ1, KCNH2 and/or SCN5A as described above), and progressive conduction disease (mutated SCN5A as described above). Diagnostic methods include analyzing the nucleic acid sequence of any or all the KCNH2 (Seq. Id. No. 6), SCN5A (Seq. Id. No. 4), KCNQ1 (Seq. Id. No. 2) genes of an individual to be tested and comparing them with the nucleic acid sequence of the native, nonvariant gene. Alternatively, the amino acid sequence of the respective polypeptides encoded by the aforelisted genes may be analyzed for the above-indicated mutations which respectively cause short QT syndrome, Brugada syndrome and/or progressive conduction disease. Pre-symptomatic diagnosis of these syndromes will enable practitioners to treat these disorders using existing medical therapy, e.g., using I$_{Kr}$ blocking agents, beta blocking agents or through electrical stimulation.

The present invention provides methods of screening the KCNH2, KCNQ1, and/or SCN5A genes to identify the mutations listed above. Such methods may include the step of amplifying the respective portions of the KCNH2, KCNQ1, and/or SCN5A genes containing and flanking the above described mutated sites, and may further include a step of providing a set of polynucleotides which are primers for amplification of said respective portions of the KCNH2, KCNQ1, and/or SCN5A genes. Methods of making such primers are well within the ordinary skill in the art. The methods are useful for identifying mutations for use in either diagnosis of short QT syndrome (mutated KCNH2 as described above), Brugada syndrome (mutated SCN5A as described above), Long QT syndrome (mutated KCNQ1, KCNH2 and/or SCN5A as described above), and progressive conduction disease (mutated SCN5A as described above) or prognosis of short QT syndrome (mutated KCNH2 as described above), Brugada syndrome (mutated SCN5A as described above), Long QT syndrome (mutated KCNQ1, KCNH2 and/or SCN5A as described above), and progressive conduction disease (mutated SCN5A as described above). The present invention is further directed to methods of screening humans for the presence of KCNH2 gene variants which cause short QT syndrome, the SCN5A variants which cause Brugada syndrome, the KCNQ1, KCNH2 and/or SCN5A variants which cause LQT syndrome, and/or the SCN5A variants which cause progressive conduction disease. Assays can be performed to screen persons for the presence of the above-described mutations in either the nucleic acid encoding the polypeptide, the polypeptide itself and/or fragments thereof. In one embodiment, the assay may be a microchip or microarray assay. The nucleic acid encoding the polypeptide and/or the polypeptide itself or a fragment thereof may also be used in assays to screen for drugs which will be useful in treating or preventing the occurrence of short QT syndrome.

The present invention also provides nucleic acid probes which will respectively and selectively hybridize to nucleic acid coding for KCNH2, KCNQ1 or SCN5A polypeptides containing the above-described mutations, for example, the mutation which causes short QT syndrome, said mutation being a substitution of lysine for asparagine at amino acid residue 588 of the KCNH2 polypeptide, but will not hybridize to DNA encoding wild type KCNH2 under hybridization conditions which only permit hybridization products to form which are fully complementary in the region of the mutation. For example, the present invention provides a nucleic acid probe which will hybridize to nucleic acid coding for a mutant KCNH2 polypeptide containing a mutation which causes short QT syndrome under conditions which only permit hybridization products to form which are fully complementary in the region causing said mutation, said mutation being caused by a mutation in said nucleic acid being a substitution of G for C or A for C at nucleotide position 1764, but will not hybridize to nucleic acid encoding wild type KCNH2 polypeptide. As used herein, "wild-type" or "WT" is the naturally occurring, non-mutant nucleic acid or protein.

The present invention also provides a method for diagnosing a polymorphism which causes short QT syndrome by hybridizing such a nucleic acid probe to a patient's sample of DNA or RNA under conditions which only permit hybridization products which are fully complementary in the region of the mutation to form, and determining the presence or absence of a signal indicating a hybridization product, the presence of a hybridization signal indicating the presence of short QT syndrome. Similarly, the present invention also provides a method for diagnosing a polymorphism which causes long QT syndrome by hybridizing such nucleic acid probes to a patient's sample of DNA or RNA under conditions which only permit hybridization products which are fully complementary in the region of the above described LQT syndrome mutations of SCN5A, KCNH2 or KCNQ1 to form, and determining the presence or absence of a signal indicating a hybridization product, the presence of a hybridization signal indicating the presence of long QT syndrome. Similarly, the present invention also provides a method for diagnosing a polymorphism which causes Brugada syndrome by hybridizing such nucleic acid probes to a patient's sample of DNA or RNA under conditions which only permit hybridization products which are fully complementary in the region of the above described Brugada syndrome mutations of SCN5A to form, and determining the presence or absence of a signal indicating a hybridization product, the presence of a hybridization signal indicating the presence of Brugada syndrome. Similarly, the present invention also provides a method for diagnosing a polymorphism which causes progressive conduction disease by hybridizing such a nucleic acid probe to a patient's sample of DNA or RNA under conditions which only permit hybridization products which are fully complementary in the region of the above described progressive conduction disease mutation of SCN5A to form, and determining the presence or absence of a signal indicating a hybridization product, the presence of a hybridization signal indicating the presence of long QT syndrome In one embodiment, the patient's DNA or RNA may be amplified and the amplified DNA or RNA is hybridized with said probes. The hybridization maybe performed in situ. A single-stranded conformation polymorphism technique may be used to assay for any of said mutations.

The present invention also provides a method for diagnosing a polymorphism which causes short QT syndrome, said polymorphism being a mutation substituting a lysine at residue 588 of the KCNH2 polypeptide, said method including using a single-stranded conformation polymorphism technique to assay for said polymorphism. The present invention also provides a method for diagnosing a polymorphism which causes Brugada syndrome, said polymorphism being at least one of the following mutations of the SCN5A polypeptide: R104W, R179 stop, T220I, G400A, E446K, F532C, A735V, R878C, H886P, L917R, E1573K, C1727R, V2321+L1307F, P336L+I1659V, Y1614 stop, deletion from E1573-G1604, and insertion of TG at 851, said method including using a single-stranded conformation polymorphism technique to assay for said polymorphism. The present invention also provides a method for diagnosing a polymorphism which causes LQT syndrome, said polymorphism being at least one of the following mutations: G189W in the KCNQ1 protein; with respect to the KCNH2 protein, R356H, a C deletion at 764, and a W398stop codon; and S1134I of the SCN5A protein, said method including using a single-stranded conformation polymorphism technique to assay for said polymorphism. The present invention also provides a method for diagnosing a polymorphism which causes progressive conduction disease, said polymorphism being a mutation substituting a serine for proline at residue 1008 of the SCN5A polypeptide, said method including using a single-stranded conformation polymorphism technique to assay for said polymorphism.

The present invention also provides a method for diagnosing a polymorphism which causes short QT syndrome comprising identifying a mismatch between a patient's DNA or RNA and a wild-type DNA or RNA probe wherein said probe hybridizes to the region of DNA encoding amino acid residue 588 of the KCNH2 polypeptide. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes Brugada syndrome comprising identifying a mismatch between a patient's DNA or RNA and wild-type DNA or RNA probes wherein said probes hybridize to the region of DNA encoding any of the following amino acid residues: 104, 179, 220, 400, 446, 532, 735, 878, 886, 917, 1573, 1727, 232, 130, 336, 1659 1614, 851 and 1573-1604 of the SCN5A polypeptide. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes long QT syndrome comprising identifying a mismatch between a patient's DNA or RNA and wild-type DNA or RNA probes wherein said probes hybridize to the region of DNA encoding any of the following amino acid residues: 189 in the KCNQ1 protein; 365, 398, and 764 in the KCNH2 protein; and 1134 of the SCN5A protein. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes progressive conduction disease comprising identifying a mismatch between a patient's DNA or RNA and a wild-type DNA or RNA probe wherein said probe hybridizes to the region of DNA encoding amino acid residue 1008 of the SCN5A polypeptide. The mismatch may be identified by an RNase assay wherein the patient's DNA or RNA, has been amplified and said amplified DNA or RNA, is hybridized with said probe. The hybridization may be performed in situ.

Also provided is a method for diagnosing a polymorphism which causes short QT syndrome which includes amplifying the region of the KCNH2 DNA or RNA surrounding and including base position 1764, and determining whether a C to A or a C to G substitution at position 1764 exists, said alteration being indicative of short QT syndrome. The present invention also provides a method for diagnosing a polymorphism which causes short QT syndrome by amplifying the region of the KCNH2 DNA or RNA encoding amino acid 588 of the KCNH2 polypeptide and sequencing the amplified DNA or RNA wherein substitution of nucleic acid encoding lysine at position 588 is indicative of short QT syndrome. Polymorphisms can lead to subclinical forms of each of these syndromes, which may manifest only after exposure to certain drugs or environmental factors. As such, the identification of a polymorphism allows practitioners to counsel patients to avoid these drugs or environmental factors.

Also provided is an isolated nucleic acid coding for a mutant KCNH2 polypeptide which causes short QT syndrome. In one embodiment, the nucleic acid encodes a mutant KCNH2 polypeptide containing a substitution of lysine for asparagine at position 588. In one embodiment, the DNA coding for a mutant KCNH2 polypeptide contains a substitution of either G or A for C at nucleotide position 1764 of the wild-type KCNH2 gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant KCNH2 polypeptide containing a substitution of lysine for asparagine at position 588.

Also provided is an isolated nucleic acid coding for a mutant SCN5A polypeptide having at least one of the following mutations: R104W, R179 stop, T220I, G400A, E446K, F532C, A735V, R878C, H886P, L917R, E1573K, C1727R, V232I+L1307F, P336L+I1659V, Y1614 stop, deletion from E1573-G1604, and insertion of TG at 851, and which causes Brugada syndrome. In one embodiment, the DNA coding for a mutant SCN5A protein contains at least one nucleotide substitution in the wild-type SCN5A gene as follows: t5179c (C1727R), c310t (R104W), insert of tg at 2550 (TG851), c2632t (R878C), t1595g (F532C), t2790g (L917R), c2204t (A735V), g4717a (E1573K), c535t (R179 stop), g1336a (E446K), g1199c (G400A), a2675c (H886P), c4842g (Y1614 stop), c659t (T220I), g694a+c3919t (V232+L1307F), splice of exons 27 and 28=4810+7 ins GGG (E1573-G1604 deletion), and c1007t+a4975g (P336L+I1659V). Vectors containing such isolated nucleic acid are also provided. Cells transformed or transfected with such isolated nucleic acid are also provided. Also provided are a nucleic acid probes which will hybridize to said isolated nucleic acid. Also provided is an isolated mutant SCN5A polypeptide containing at least one of the following mutations: R104W, R179 stop, T220I, G400A, E446K, F532C, A735V, R878C, H886P, L917R, E1573K, C1727R, V232I+L1307F, P336L+I1659V, Y1614 stop, deletion from E1573-G1604, and insertion of TG at 851.

Also provided is an isolated nucleic acid coding for a KCNQ1 protein mutant G189W which causes LQT syndrome. In one embodiment, the DNA coding for a mutant KCNQ1 protein contains a g165t nucleotide substitution in the wild-type KCNQ1 gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant KCNQ1 polypeptide containing a G189W mutation.

Also provided is an isolated nucleic acid coding for a mutant KCNH2 protein which causes LQT syndrome having at least one of the following mutations: R356H, a C deletion at 764, and a W398stop. In one embodiment, the DNA coding for a mutant KCNH2 protein contains at least one of the following mutations g1067a (R356H), c229I deletion (C764 deletion), and g1193a (W398 stop) of the wild-type KCNH2 gene. Vectors containing such isolated nucleic acid are also provided. Cells transformed or transfected with such isolated nucleic acid are also provided. Also provided is a nucleic acid probe which will hybridize to said isolated nucleic acid. Also provided is an isolated mutant KCNH2 polypeptide containing at least one of the following mutations: R356H, a C deletion at 764, and a W398stop.

Also provided is an isolated nucleic acid coding for a mutant SCN5A protein which causes LQT syndrome having the following mutation: S1134I. In one embodiment, the DNA coding for a mutant SCN5A protein contains a nucleotide substitution of g3401t in the wild-type SCN5A gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant SCN5A polypeptide containing a S134I mutation.

Also provided is an isolated nucleic acid coding for a mutant SCN5A protein which causes progressive conduction disease having the following mutation: P1008S. In one embodiment, the DNA coding for a mutant SCN5A protein contains a nucleotide substitution of c3022t in the wild-type SCN5A gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant SCN5A polypeptide containing a P1008S mutation.

"Isolated", as used herein, means that the original material to which it refers was removed from the environment where it may have originally been found. "Isolated" material also includes material which may have originally been found in a native environment but was synthesized outside that native environment by artificial means. Such "isolated" materials may be combined with other materials. Thus, for example, an "isolated" nucleic acid is still considered to be "isolated" even if it is found in a self-replicating cell that is the progeny of a parent cell that was transformed or transfected with nucleic acid that was not native to that parent cell.

Figure 2:
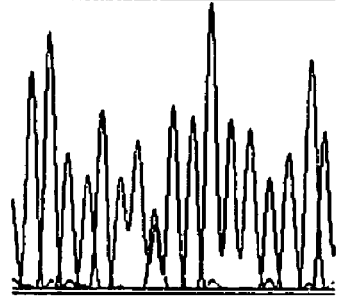
FIG. 2 illustrates DNA sequencing analysis of with a C to A (family 30-371) and a C to G (family 30-335) substitution in exon 7 of KCNH2. This results in the same amino acid substitution of lysine for asparagine at codon 588 (N588K).
Figure 2:
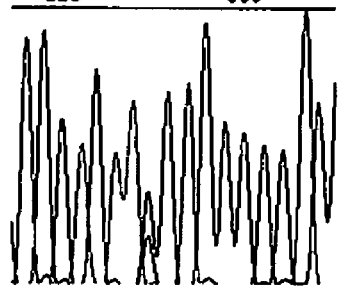
Figure 2:
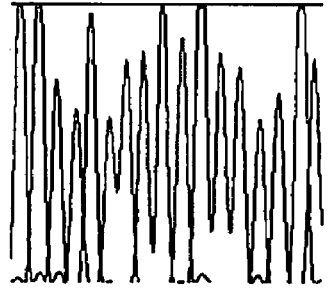

With respect to short QT syndrome, two families with hereditary short QT syndrome and a high incidence of ventricular arrhythmias and sudden cardiac death were studied. Analysis for the genetic mutation in these two families was performed. (Families 30-371 and 30-335) (FIG. 1). Highly informative chromosomal markers were used targeting loci containing 24 candidate genes involved in cardiac electrical activity to perform the initial haplotype analysis in family 30-371. Direct sequencing of the gene exons corresponding to the loci segregating with the affected individuals identified a missense mutation (C to A substitution at nucleotide 1764) in family 30-371 in KCNH2. Analysis of family 30-335 identified a different missense mutation in the same residue (C to G substitution at nucleotide 1764) in KCNH2. Both mutations substituted the asparagine at codon 588 in KCNH2 protein (HERG) for a positively charged lysine (FIG. 2). This residue corresponds to exon 7, which encodes the pore region of the $I_{Kr}$ channel. This residue is located in the S5-P loop region of HERG at the mouth of the channel. The mutation was present in all affected members in the respective family and in none of the unaffected. Given the pattern of transmission, it is believed that the mutation must have been present in two of the individuals who died suddenly in family 30-371 as obligate carriers. These mutations were not present in four hundred control chromosomes. A third family line with certain members exhibiting sudden cardiac death mortality was investigated and also found to have the N588K mutation in KCNH2 associated with SQT syndrome.

To determine the mechanism by which mutation N588K reduces the duration of the ventricular action potential and shortens the QT interval and to obtain current recordings representative of $I_{Kr}$, the mutated KCNH2 channels (N588K) were co-expressed with the ancillary β-subunit KCNE2 (MiRP1) in human embryonic kidney cells (TSA201) and patch clamp experiments were performed. Whole cell recordings (FIG. 3a) showed that the wild type (WT) HERG/KCNE2 currents elicited by sequential depolarizing pulses reached a maximum steady state current at −5 mV and started to decrease due to the rapid onset of inactivation (rectification) at more positive potentials. In cells transfected with the WT channels, the typical large tail currents generated by inactivated channels rapidly reopening (recovery) upon repolarization were also observed. In contrast, N588K/KCNE2 steady state current continued to increase linearly well over +40 mV and significant tail currents following repolarization were not observed. Analysis of the current voltage relationship (FIG. 3B) shows that N588K/KCNE2 currents did not rectify significantly in a physiological range of potentials.

Figure 3:
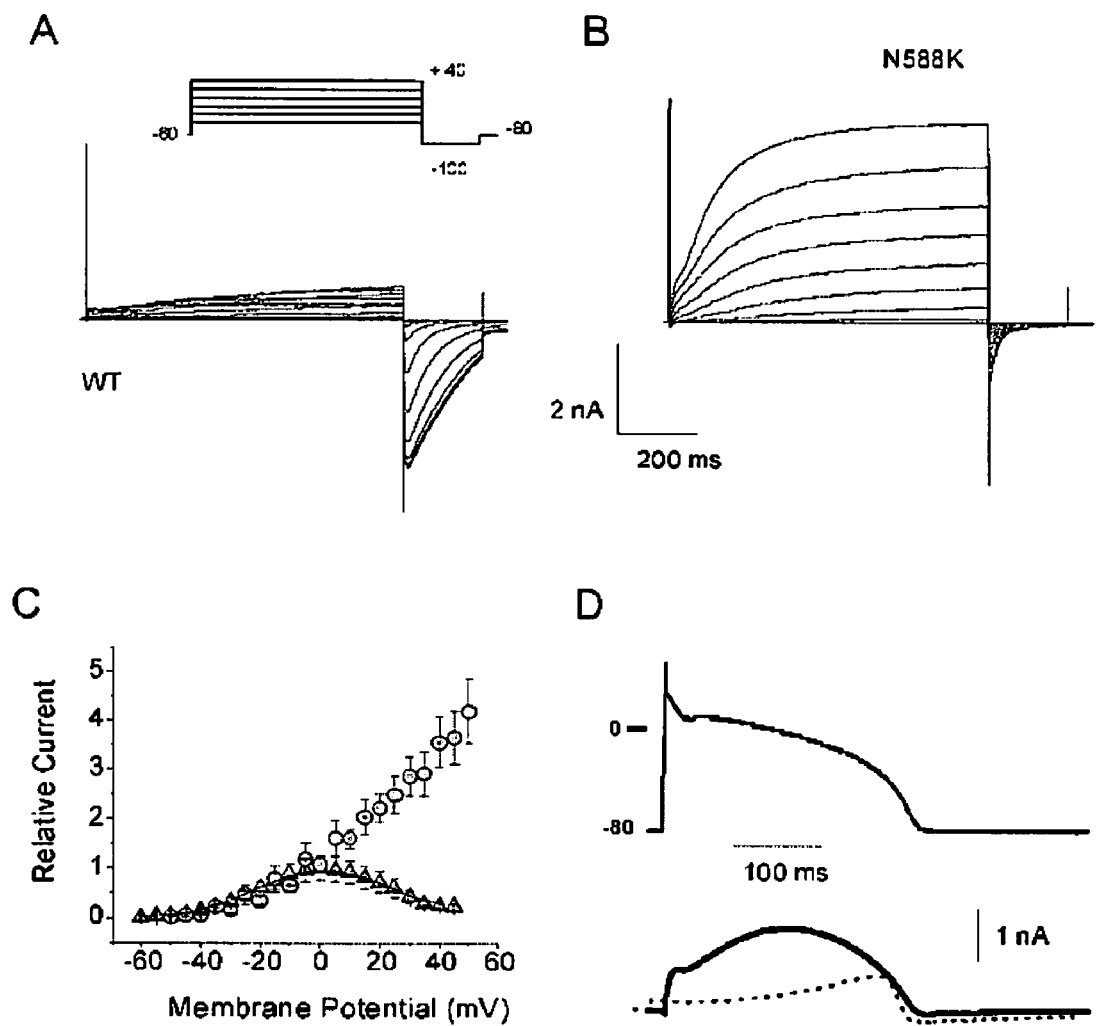
FIG. 3 illustrates mutation N588K removed inactivation of KCNH2. A) Series of wild type KCNH2/KCNE2 currents elicited by 800 ms depolarizing pulses in increments of 10 mV between −50 and 50 mV from a holding potential of −80 mV. A large tail inward current is observed upon repolarization to −100 mV. B) Same protocol as in A applied on TSA201 cells transfected with the mutant channel N588K. Developing currents are dramatically increased due to loss of rectification properties of the channel and the tail currents were abolished by the mutation. C) Normalized current voltage relationship. Current amplitude was normalized to the value at 0 mV (maximum for WT). D) Currents recorded during an action potential clamp. Dotted line: WT, solid line: N588K. N588K thus leads to a dramatic gain of function in IKr

To determine how the mutation altered the kinetics of the current during an action potential, WT and N588K currents were elicited using a stimulus generated by a previously recorded AP. FIG. 3C shows that WT currents displayed a "hump" like waveform with slow activation kinetics and a rapid increase during the repolarization phase of the action potential, as inactivated channels quickly recovered. In sharp contrast, N588K/KCNE2 currents displayed a dome-like configuration resulting in a much larger relative current during the initial phases of the action potential.

KCNH2 protein has a "shaker like" tetrameric structure composed of homologous core units each containing six membrane-spanning segments. Co-assembly with the beta-subunit MiRP1 (KCNE2) is required to fully reproduce the biophysical and pharmacological properties of the native $I_{Kr}$. KCNH2 has previously been linked to a decrease in outward repolarizing current responsible for the hereditary (LQT2) and acquired forms of LQTS. A common polymorphism in KCNH2 (K897T) has been reported to produce a modest abbreviation of QTc to 388.5±2.9 by shifting the voltage of activation of $I_{Kr}$ by −7 mV. KCNH2 is also the primary target of Class III antiarrhythmics. Binding of dofetilide and sotalol occurs primarily in the open state. The S5-P loop region of KCNH2 forms the pore of the channel and contains the selectivity filter. Chimeric studies of KCNH2 showed that replacing the S5-S6 linker, which contains the pore region, by the corresponding area from the bovine ether-a-go-go (BEAG) removes the high affinity block by dofetilide, indicating that this area contains residues important for binding of methanesulfonanilides and C type inactivation. Abolition of the current rectification by N588K further support the notion that residues in this area of the channel are important for C-type inactivation and binding of methanesulfonanilides to KCNH2. Block of $I_{Kr}$ by methanesulfonanilides, phosphodiesterase inhibitors, macrolide antibiotics, antifungal agents and antihistamines is the basis for the QT prolonging effects and potential arrythmogenecity of these compounds.

Figure 4:
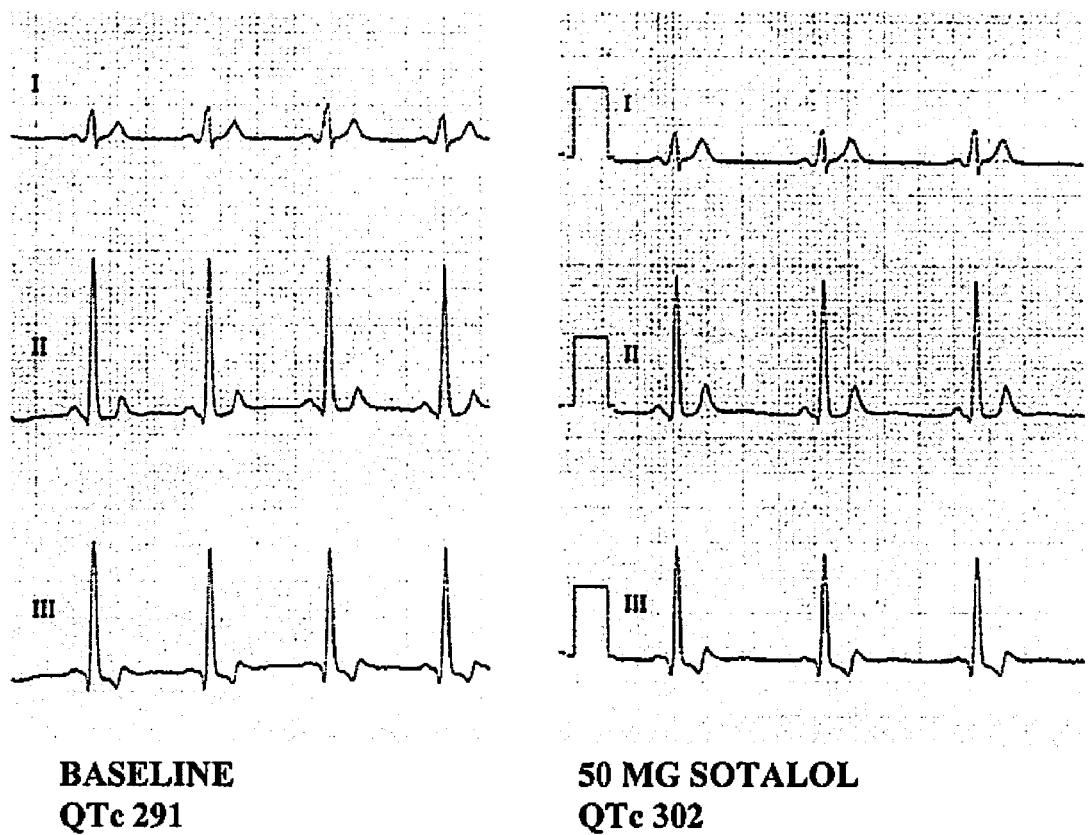
FIG. 4 illustrates an electrocardiogram of patient IV-5 before and after the administration of Sotalol 1 mg/kg body weight intravenously. Electrocardiogram shows leads I to III at 25 mm/s. QTc changes minimally from 291 to 302 msec.
Figure 5:
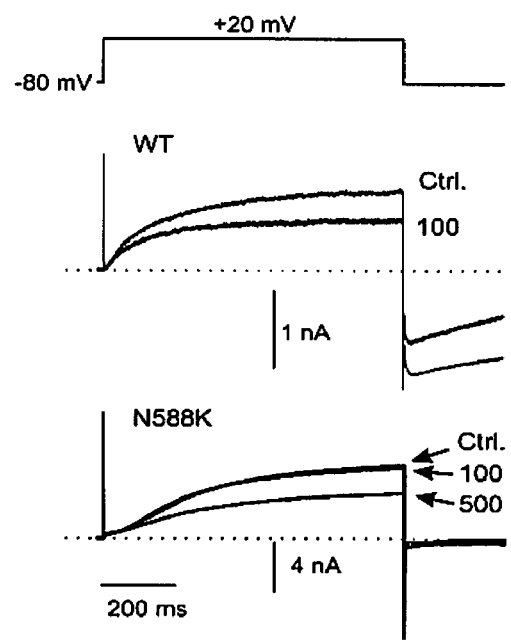
FIG. 5 illustrates the effect of sotalol on KCNH2 currents in human embryonic kidney cells (TSA201) transformed with WT KCNH2/KCNE2 compared with TSA201 cells transformed with N588K KCNH2/KCNE2 using patch clamp experiments. Recordings of WT and N588K currents during a 800-ms pulse to +20 mV (Vh=−80 mV) repeated every 15 seconds in control and 10 min after addition of 100 and 500 μM D-sotalol. Concentration-response relation is represented graphically for WT and N588K currents are expressed as percent of control values following application of D-sotalol. Data: Mean±SEM (n=4-6 cells for each point). IC$_{50}$ is shifted from 0.137 mM in WT to 2.82 mM in the N588K mutant. The N588K mutation reduced sensitivity to sotalol by 20-fold.
Figure 5:
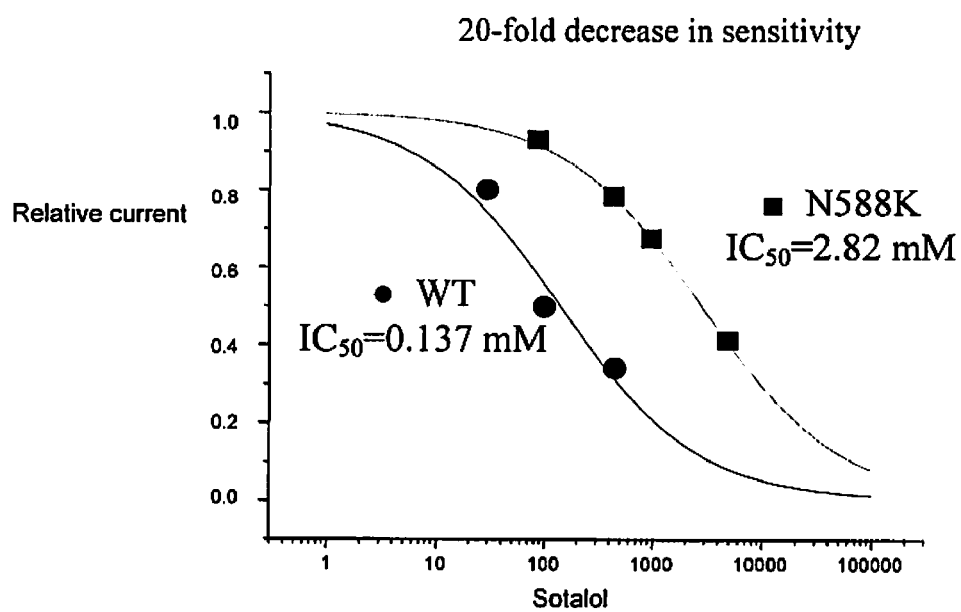
Figure 6:
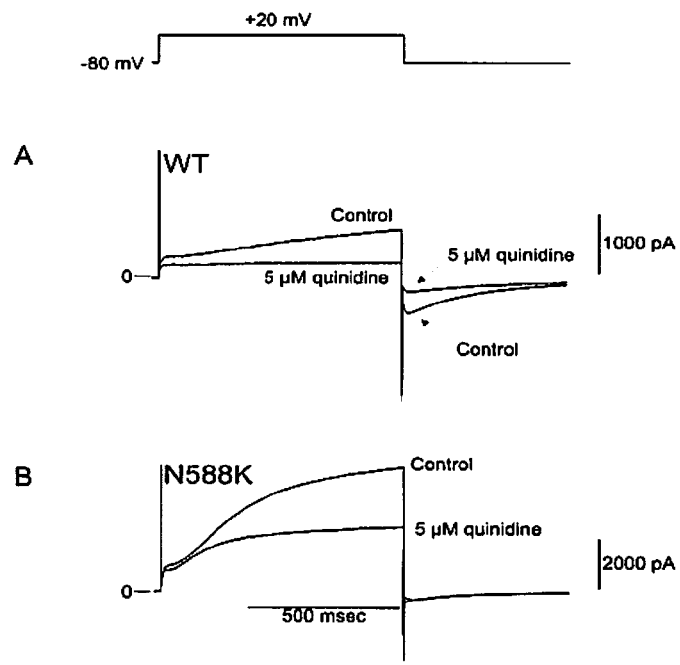
FIG. 6 illustrates the effect of quinidine on KCNH2 currents in human embryonic kidney cells (TSA201) transformed with WT KCNH2/KCNE2 compared with TSA201 cells transformed with N588K KCNH2/KCNE2 using patch clamp experiments. Recordings of WT and N588K currents during a 800-ms pulse to +20 mV (Vh=−80 mV) repeated every 15 seconds in control and 10 min after addition of 5 μM quinidine. Dose-response relation is represented graphically for WT and N588K currents are expressed as percent of control values following application of quinidine. Data: Mean±SEM (n=4-6 cells for each point). IC$_{50}$ is shifted from 0.75 mM in WT to 4.35 mM in the N588K mutant. The N588K mutation reduced sensitivity to quinidine by 5.8 fold.
Figure 6:
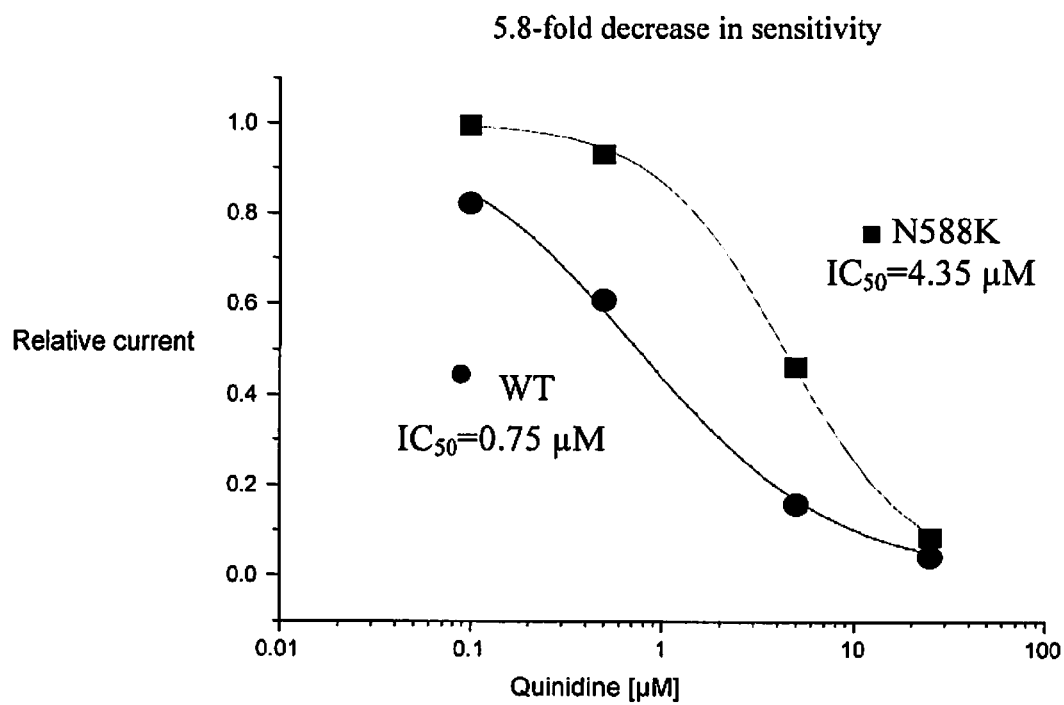

Because QT abbreviation is likely due to a decrease in ventricular AP duration subsequent to an increase in repolarizing current, it was believed that blocking $I_{Kr}$ with Class III antiarrhythmic drugs could be a potential therapeutic approach to the treatment of SQTS. FIG. 4 shows that Sotalol, a class III antiarrhythmic with potent $I_{Kr}$ blocking actions, was administered as a preliminary test of this hypothesis. FIG. 4 illustrates the response of patient IV-5 of family 30-371 to 1 mg/kg IV sotalol. QTc at baseline was 291 msec and remained practically unchanged after sotalol, suggesting that this particular phenotype is not responsive to this dose of the $I_{Kr}$ blocker. FIG. 5 shows that extracellular application of sotalol caused a shift in sensitivity of the KCNH2 channel by 20 fold as a consequence of the N588K mutation in TSA201 cells. $IC_{50}$ was shifted from 0.137 mM in WT to 2.82 mM in N588K. FIG. 6 shows that extracellular application of quinidine caused a shift in sensitivity of the KCNH2 channel by 5.8 fold as a consequence of the N588K mutation in TSA201 cells. $IC_{50}$ was shifted from 0.75 mM in WT to 4.35 mM in N588K. Accordingly, the N588K mutation produces less sensitivity of a decrease in sensitivity of KCNH2 to quinidine.

These results provide for the first time a genetic basis for the short QT syndrome, a disease characterized by marked abbreviation of the QT interval and a high incidence atrial and ventricular arrhythmias and sudden death. The data demonstrate the first linkage of a cardiac disease to a gain of function in KCNH2, which encodes for rapidly activating delayed rectifier current, $I_{Kr}$. A N588K missense mutation is shown to abolish rectification of the current and reduce the affinity of the channel for drugs with Class III antiarrhythmic action. The net effect of the mutation is to increase the repolarizing currents active during the early phases of the AP, leading to abbreviation of the action potential, and thus to abbreviation of the QT interval. Because of the heterogeneous distribution of ion currents within the heart, it may be that the AP shortening in SQTS is heterogeneous, leading to accentuation of dispersion of repolarization and the substrate for the development of both atrial and ventricular arrhythmias. Given the young age of some patients (3 months), the data also provides evidence linking KCNH2 mutations to sudden infant death syndrome (SIDS). Since $I_{Ks}$ contributes importantly to repolarization, block of this current may benefit SQT syndrome. Selective $I_{Ks}$ blockers are under development, e.g., Chromanol 293B and HMR 1556. When compared to Chromanol 293B, HMR 1556 has a higher potency and specificity towards $I_{Ks}$.

Accordingly, a method of screening compounds for use in treating cardiac ion channel abnormalities resulting from the mutations described herein is provided. In one aspect, patients who have been diagnosed with one or more of the mutations described herein are dosed with a pharmaceutically acceptable compound which an investigator suspects may have an effect on the ion channel, an electrocardiogram is taken, and the effect of the QT interval, if any, is ascertained. A therapeutic effect is considered one which modifies an abnormal interval to a more normal interval.

In another aspect, a cell based assay is provided. Cells containing nucleic acid encoding mutant KCNH2, SCN5A or KCNQ1 protein as described herein are contacted with a test compound and the effect on ion channel currents is ascertained. Suitable cells include, e.g., human embryonic kidney cells (HEK) and cardiac cell lines such as HL-1, described in U.S. Pat. No. 6,316,207, incorporated herein by reference. Other modalities include transfected oocytes or transgenic animals. A test compound is added to the cells in culture or administered to a transgenic animal containing mutant KCNH2, SCN5A or KCNQ1 and the effect on the current of the ion channel is compared to the current of a cell or animal containing the wild-type KCNH2, SCN5A or KCNQ1. Drug candidates which alter the current to a more normal level are useful for treating or preventing LQT syndrome, SQT syndrome, Brugada syndrome or progressive conduction disease.

Figure 7:
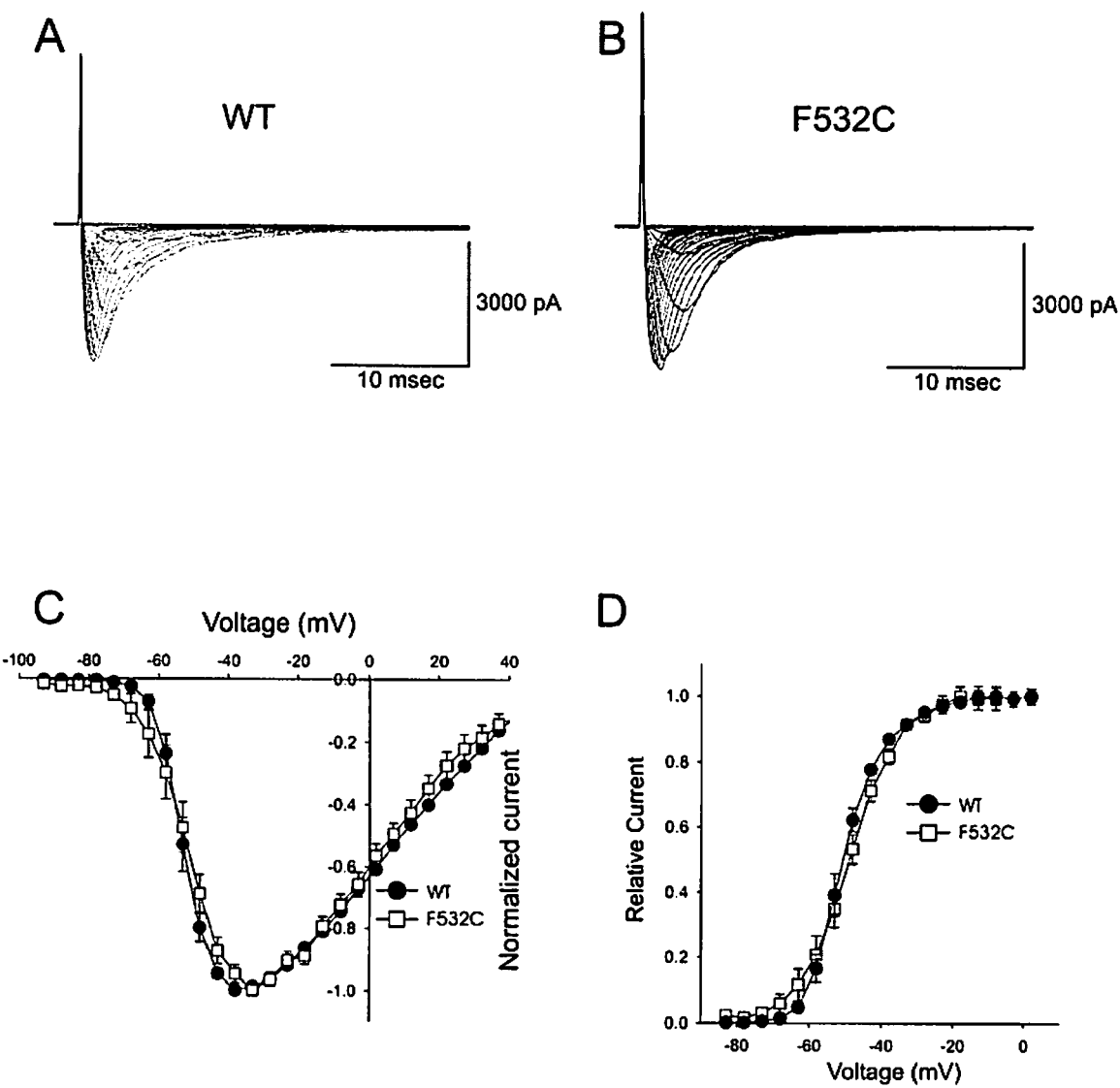
FIG. 7 illustrates representative whole cell current recordings for WT (Panel A) and SCN5A F532C Brugada syndrome mutant (Panel B) in transfected TSA201 cells. Current recordings were obtained at test potentials between −100 and 0 mV in 5 mV increments from a holding potential of −120 mV. Panel C: Normalized I-V relation for WT (n=9) and F532C (n=9) channels. Panel D: Steady state-activation relation for WT and F532C. Chord conductance was determined using the ratio of current to the electromotive potential for the 9 cells shown in Panel C. Data were normalized and plotted against their test potential.

FIG. 7 illustrates representative whole cell current recordings for WT (Panel A) and SCN5A F532C Brugada syndrome mutant (Panel B) in transfected TSA201 cells. Current recordings were obtained at test potentials between −100 and 0 mV in 5 mV increments from a holding potential of −120 mV. Panel C: Normalized I-V relation for WT (n=9) and F532C (n=9) channels. Panel D: Steady state-activation relation for WT and F532C. Chord conductance was determined using the ratio of current to the electromotive potential for the 9 cells shown in Panel C. Data were normalized and plotted against their test potential.

Figure 8:
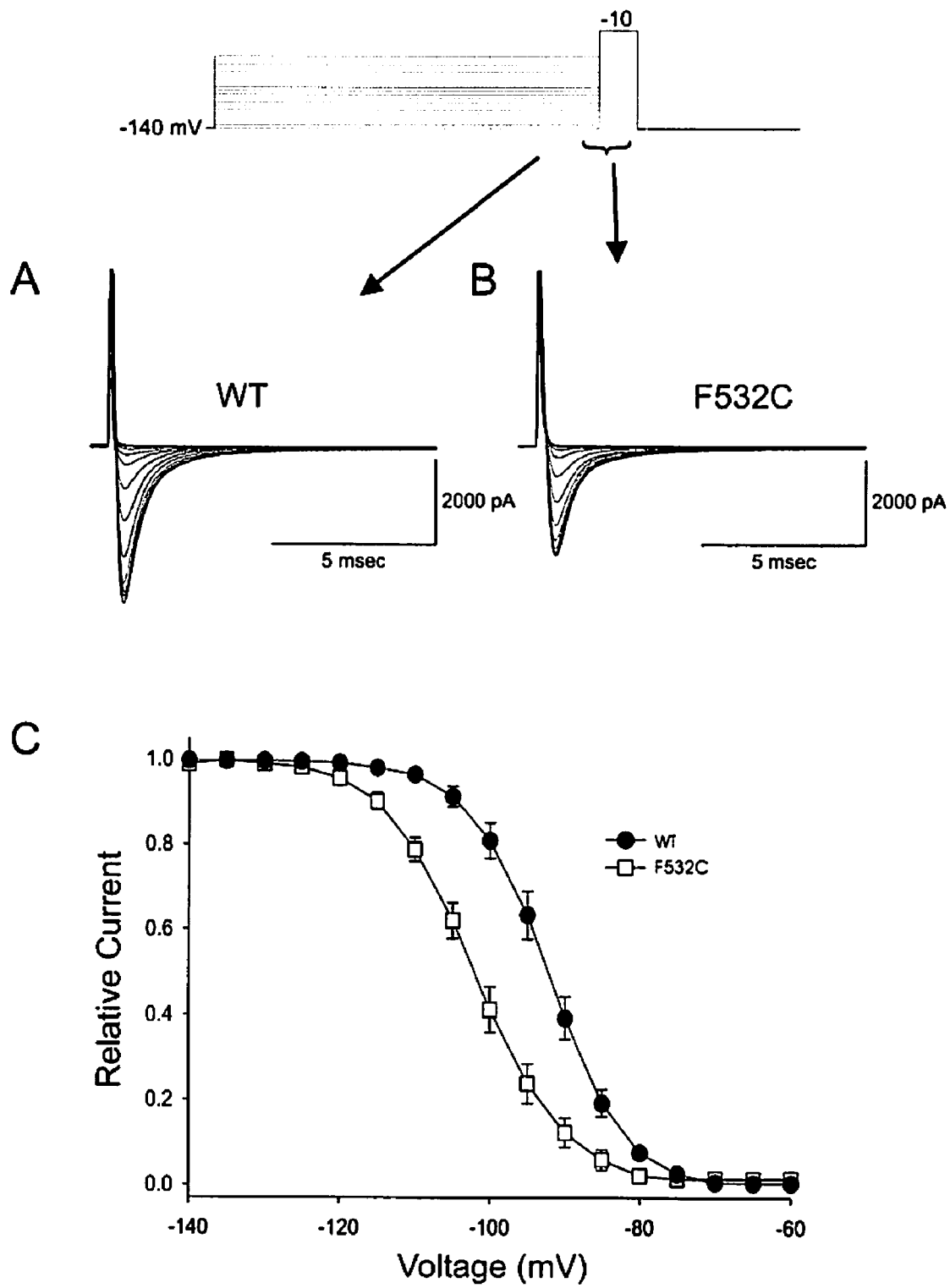
FIG. 8 illustrates representative steady-state inactivation recordings for wild-type (WT) (Panel A) and SCN5A F532C (Panel B) observed in response to the voltage clamp protocol (top of figure). Panel C: Peak current was normalized to their respective maximum values and plotted against the conditioning potential. The steady state inactivation relation measured with the F532C mutation shows a −10 mV shift of mid-inactivation voltage in the hyperpolarizing direction (−102.4±4.8; n=9 versus −92.3±2.4 for WT; n=10; P<0.05).

FIG. 8 illustrates representative steady-state inactivation recordings for WT (Panel A) and SCN5A F532C (Panel B) observed in response to the voltage clamp protocol (top of figure). Panel C: Peak current was normalized to their respective maximum values and plotted against the conditioning potential. The steady state inactivation relation measured with the F532C mutation shows a −10 mV shift of mid-inactivation voltage in the hyperpolarizing direction (−102.4±4.8; n=9 versus −92.3±2.4 for WT; n=10; P<0.05). Thus, a major loss of function of sodium channel current is expected consistent with the phenotype of the disease. Such a shift would be expected to lead to a reduced sodium channel current due to reduced availability of sodium channels at the normal resting potential.

According to the diagnostic and prognostic methods of the present invention, alteration of the wild-type KCNH2, KCNQ1, and/or SCN5A genes and/or proteins are detected. Useful diagnostic techniques include, but are not limited to fluorescent in situ hybridization (FISH), direct nucleic acid sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP. Also useful is the recently developed technique of DNA microarray technology. Implementation of these techniques is considered to be routine for those skilled in the art.

The presence of sudden cardiac death or susceptibility thereto may be ascertained by testing any tissue of a human subject or non-human subject for mutations of the KCNH2, KCNQ1, and/or SCN5A genes as described herein. For example, a person who has inherited a germline KCNH2, KCNQ1, and/or SCN5A mutation as described herein would be prone have SQT syndrome, LQT syndrome, Brugada syndrome, progressive transmission disease, to develop arrhythmias or suffer from sudden cardiac death depending on the particular mutation. This can be determined by testing DNA from any tissue of the subject's body. Most simply, blood can be drawn and DNA extracted from the cells of the blood. In addition, prenatal diagnosis can be accomplished by testing fetal cells, placental cells or amniotic cells for mutations of the KCNH2, KCNQ1, and/or SCN5A genes. Alteration of a wild-type KCNH2, KCNQ1, and/or SCN5A genes, whether, for example, by point mutation or deletion, can be detected by any of the means discussed herein.

Those skilled in the art are familiar with numerous methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., Proc. Natl. Acad. Sci. USA 86:2766-2770 (1989)). This method does not detect all sequence changes, especially if the DNA fragment size is greater than 200 bp, but can be optimized to detect most DNA sequence variation. The reduced detection sensitivity may be a disadvantage, but the increased throughput possible with SSCP can make it an attractive, viable alternative to direct sequencing for mutation detection. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., Am. J. Hum. Genet. 49:699-706 (1991)), heteroduplex analysis (HA) (White et al., Genomics 12:301-306 (1992)) and chemical mismatch cleavage (CMC) (Grompe et al., Proc. Natl. Acad. Sci. USA 86:5855-5892 (1989)). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., Science 277:1078-1081 (1997)).

Detection of point mutations described herein may be accomplished by molecular cloning of the KCNH2, KCNQ1, and/or SCN5A genes and sequencing the genes using techniques well known in the art. Also, the gene or portions of the gene may be amplified, e.g., by PCR or other amplification technique, and the amplified gene or amplified portions of the gene may be sequenced.

Well known methods for indirect, test for confirming the presence of a susceptibility mutant include: 1) single stranded conformation analysis (SSCP) (Orita M, et al. (1989) Proc. Natl. Acad. Sci. USA 86:2766-2770); 2) denaturing gradient gel electrophoresis (DGGE) (Wartell R M, et al. (1990) Nucl. Acids Res. 18:2699-2705; Sheffield V C, et al. (1989) Proc. Natl. Acad. Sci. USA 86:232-236); 3) RNase protection assays (Finkelstein J, et al. (1990) Genomics 7:167-172; Kinszler K W, et al. (1991) Science 251:1366-1370); 4) allele-specific oligonucleotides (ASOs) (Conner B J, et al. (1983) Proc. Natl. Acad. Sci. USA 80:278-282); 5) the use of proteins which recognize nucleotide mismatches, such as the E. coli mutS protein (Modrich P (1991) Ann. Rev. Genet. 25:229-253); and 6) allele-specific PCR (Ruano G and Kidd K K (1989) Nucl. Acids Res. 17:8392). For allele-specific PCR, primers are used which hybridize at their 3' ends to particular KCNH2, KCNQ1, and/or SCN5A gene mutations. If the particular mutation is not present, an amplification product is not observed. Amplification Refractory Mutation System (ARMS) can also be used. In addition, restriction fragment length polymorphism (RFLP) probes for the genes or surrounding marker genes can be used to score alteration of an mutant or an insertion in a polymorphic fragment. Such a method is useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences. Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. The method involves the use of a labeled riboprobe which is complementary to the respective human wild-type KCNH2, KCNQ1, and/or SCN5A gene coding sequences. The riboprobe and either MRNA or DNA isolated from the subject are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the MRNA or gene, it will be desirable to use a number of these probes to screen the whole MRNA sequence for mismatches.

In similar fashion, DNA probes can be used to detect mismatches, through enzymatic or chemical cleavage. See, e.g., Cotton R G, et al. (1988) Proc. Natl. Acad. Sci. USA 85:4397-4401; Shenk T E, et al. (1975) Proc. Natl. Acad. Sci. USA 72:989-993; Novack D F, et al. (1986) Proc. Natl. Acad. Sci USA 83:586-590. Alternatively, mismatches can be detected by shifts in the electrophoretic mobility of mismatched duplexes relative to matched duplexes. See, e.g., Cariello N F (1988) Am. J. Human Genetics 42:726-734). With either riboprobes or DNA probes, the cellular mRNA or DNA which might contain a mutation can be amplified using PCR before hybridization. Changes in DNA of the KCNH2, KCNQ1, and/or SCN5A genes can also be detected using Southern hybridization.

DNA sequences of the KCNH2, KCNQ1, and/or SCN5A genes which have been amplified by use of PCR may also be screened using mutant-specific probes. These probes are nucleic acid oligomers, each of which contains a region of the gene sequence harboring any of the mutations described herein. For example, one oligomer may be about 30 nucleotides in length, corresponding to a portion of the gene sequence. By use of a battery of such probes, PCR amplification products can be screened to identify the presence of a previously identified mutation in the gene. Hybridization of probes with amplified KCNH2, KCNQ1, and/or SCN5A sequences can be performed, for example, on a nylon filter. Hybridization to a particular probe under high stringency hybridization conditions indicates the presence of the same mutation in the tissue as in the allele-specific probe. High stringency hybridization conditions may be defined as those conditions which allow an 8 basepair stretch of a first nucleic acid (a probe) to bind to a 100% perfectly complementary 8 basepair stretch of nucleic acid while simultaneously preventing binding of said first nucleic acid to a nucleic acid which is not 100% complementary, i.e., binding will not occur if there is a mismatch.

Thus, in one embodiment, the above-identified DNA sequences may be detected by DNA hybridization probe technology. In one example, which is not exclusive, the sample suspected of containing the genetic marker is spotted directly on a series of membranes and each membrane is hybridized with a different labeled oligonucleotide probe that is specific for the particular sequence variation. One procedure for spotting the sample on a membrane is described by Kafotos et al., Nucleic Acids Research, 7:1541-1552 (1979).

Briefly, the DNA sample affixed to the membrane may be pretreated with a prehybridization solution containing sodium dodecyl sulfate, Ficoll, serum albumin and various salts prior to the probe being added. Then, a labeled oligonucleotide probe that is specific to each sequence to be detected is added to a hybridization solution similar to the prehybridization solution. The hybridization solution is applied to the membrane and the membrane is subjected to hybridization conditions that will depend on the probe type and length, type and concentration of ingredients, etc. Generally, hybridization may be carried out at about 25-75° C., preferably 35 to 65° C., for 0.25-50 hours, preferably less than three hours. The greater the stringency of conditions, the greater the required complementarity for hybridization between the probe and sample. If the background level is high, stringency may be increased accordingly. The stringency can also be incorporated in the wash.

After the hybridization the sample is washed of unhybridized probe using any suitable means such as by washing one or more times with varying concentrations of standard saline phosphate EDTA (SSPE) (180 nM NaCl, 10 mM $Na_2$ $HPO_4$ and 1 M EDTA, pH 7.4) solutions at 25-75° C. for about 10 minutes to one hour, depending on the temperature. The label is then detected by using any appropriate detection techniques known to those skilled in the art.

The sequence-specific oligonucleotide that may be employed herein is an oligonucleotide that may be prepared using any suitable method, such as, for example, the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared that can then be joined together to form longer nucleic acids. For a description of this method, see, e.g., Narang, S. A., et al., Meth. Enzymol., 68, 90 (1979) and U.S. Pat. No. 4,356,270.

A second type of organic synthesis is the phosphodiester method, which has been utilized to prepare tRNA genes. See Brown, E. L., et al., Meth. Enzymol., 68, 109 (1979) for a description of this method. As in the phosphotriester method, the phosphodiester method involves synthesis of oligonucleotides that are subsequently joined together to form the desired nucleic acid.

Automated embodiments of these methods may also be employed. In one such automated embodiment diethylphosphoramidites are used as starting materials and may be synthesized as described by Beaucage et al., Tetrahedron Letters, 22:1859-1862 (1981). One method for synthesizing oligonucleotides on a modified solid support is described, e.g., in U.S. Pat. No. 4,458,066. It is also possible to use a primer which has been isolated from a biological source (such as a restriction endonuclease digest).

The sequence-specific oligonucleotide must encompass the region of the sequence which spans the nucleotide variation being detected and must be specific for the nucleotide variation being detected. For example, oligonucleotides may be prepared, each of which contains the nucleotide sequence site characteristic of each of the mutated DNA sequences herein. Each oligonucleotide would be hybridized to duplicates of the same sample to determine whether the sample contains one or more of the regions of the locus where the mutations described herein may occur which are characteristic of LQT syndrome, SQT syndrome, Brugada syndrome and progressive conduction disease.

The length of the sequence-specific oligonucleotide will depend on many factors, including the source of oligonucleotide and the nucleotide composition. For purposes herein, the oligonucleotide typically contains 15-30 nucleotides, although it may contain more or fewer nucleotides. While oligonucleotides which are at least 19-mers in length may enhance specificity and/or sensitivity, probes which are less than 19-mers, e.g., 16-mers, show more sequence-specific discrimination, presumably because a single mismatch is more destabilizing. If amplification of the sample is carried out as described below prior to detection with the probe, amplification increases specificity so that a longer probe length is less critical, and hybridization and washing temperatures can be lowered for the same salt concentration. Therefore, in such a case it may be preferred to use probes which are less than 19-mers.

Where the sample is first placed on the membrane and then detected with the oligonucleotide, the oligonucleotide should be labeled with a suitable label moiety, which may be detected by spectroscopic, photochemical, biochemical, immunochemical or chemical means. Immunochemical means include antibodies which are capable of forming a complex with the oligonucleotide under suitable conditions, and biochemical means include polypeptides or lectins capable of forming a complex with the oligonucleotide under the appropriate conditions. Examples include fluorescent dyes, electron-dense reagents, enzymes capable of depositing insoluble reaction products or being detected chronogenically, such as alkaline phosphatase, a radioactive label such as $^{32}P$, or biotin. If biotin is employed, a spacer arm may be utilized to attach it to the oligonucleotide.

In a "reverse" dot blot format, a labeled sequence-specific oligonucleotide probe capable of hybridizing with one of the DNA sequences is spotted on (affixed to) the membrane under prehybridization conditions as described above. The sample is then added to the pretreated membrane under hybridization conditions as described above. Then the labeled oligonucleotide or a fragment thereof is released from the membrane in such a way that a detection means can be used to determine if a sequence in the sample hybridized to the labeled oligonucleotide. The release may take place, for example, by adding a restriction enzyme to the membrane which recognizes a restriction site in the probe. This procedure, known as oligomer restriction, is described more fully in EP Patent Publication 164,054 published Dec. 11, 1985, the disclosure of which is incorporated herein by reference.

Alternatively, a sequence specific oligonucleotide immobilized to the membrane could bind or "capture" a target DNA strand (PCR-amplified). This "captured" strand could be detected by a second labeled probe. The second oligonucleotide probe could be either locus-specific or allele-specific.

In an alternative method for detecting the DNA sequences herein, the sample to be analyzed is first amplified using DNA polymerase, nucleotide triphosphates and primers. Briefly, this amplification process involves the steps of:

(a) treating a DNA sample suspected of containing one or more of the mutations described above, together or sequentially, with different nucleotide triphosphates, an agent for polymerization of the nucleotide triphosphates, and one deoxyribonucleotide primer for each strand of each DNA suspected of containing the abode described mutations under hybridizing conditions, such that for each DNA strand containing each different genetic marker to be detected, an extension product of each primer is synthesized which is complementary to each DNA strand, wherein said primer(s) are selected so as to be substantially complementary to each DNA strand containing each different genetic marker, such that the extension product synthesized from one primer, when it is separated from its complement, can serve as a template for synthesis of the extension product of the other primer; (b) treating the sample under denaturing conditions to separate the primer extension products from their templates if the sequence(s) to be detected are present; and (c) treating the sample, together or sequentially, with the nucleotide triphosphates, an agent for polymerization of the nucleotide triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence(s) if present.

The sample is then affixed to a membrane and detected with a sequence-specific probe as described above. Preferably, steps (b) and (c) are repeated at least five times, and more preferably 15-30 times if the sample contains human genomic DNA. If the sample comprises cells, preferably they are heated before step (a) to expose the DNA therein to the reagents. This step avoids extraction of the DNA prior to reagent addition.

In a "reverse" dot blot format, at least one of the primers and/or at least one of the nucleotide triphosphates used in the amplification chain reaction is labeled with a detectable label, so that the resulting amplified sequence is labeled. These labeled moieties may be present initially in the reaction mixture or added during a later cycle. Then an unlabeled sequence-specific oligonucleotide capable of hybridizing with the amplified sequence(s), if the sequence(s) is/are present, is spotted on (affixed to) the membrane under prehybridization conditions as described above. The amplified sample is then added to the pretreated membrane under hybridization conditions as described above. Finally, detection means are used to determine if an amplified sequence in the DNA sample has hybridized to the oligonucleotide affixed to the membrane. Hybridization will occur only if the membrane-bound sequence containing the variation is present in the amplification product.

Variations of this method include use of an unlabeled PCR target, an unlabeled immobilized allele-specific probe and a labeled oligonucleotide probe in a sandwich assay.

The amplification method provides for improved specificity and sensitivity of the probe; an interpretable signal can be obtained with a 0.04 µg sample in six hours. Also, if the amount of sample spotted on a membrane is increased to 0.1-0.5 µg, non-isotopically labeled oligonucleotides may be utilized in the amplification process rather than the radioactive probes used in previous methods. Finally, as mentioned above, the amplification process may be applicable to use of sequence-specific oligonucleotides less than 19-mers in size, thus allowing use of more discriminatory sequence-specific oligonucleotides.

In a variation of the amplification procedure, a thermostable enzyme, such as one purified from Thermus aquaticus, may be utilized as the DNA polymerase in a temperature-cycled chain reaction. The thermostable enzyme refers to an enzyme which is stable to heat and is heat resistant and catalyzes (facilitates) combination of the nucleotides in the proper manner to form the primer extension products that are complementary to each DNA strand.

In this latter variation of the technique, the primers and nucleotide triphosphates are added to the sample, the mixture is heated and then cooled, and then the enzyme is added, the mixture is then heated to about 90-100° C. to denature the DNA and then cooled to about 35-40° C., and the cycles are repeated until the desired amount of amplification takes place. This process may also be automated. The amplification process using the thermostable enzyme is described more fully in U.S. Pat. No. 4,965,188, which is incorporated herein by reference.

The invention herein also contemplates a kit format which includes a packaged multicontainer unit having containers for each labeled sequence-specific DNA probe. The kit may optionally contain a means to detect the label (such as an avidin-enzyme conjugate and enzyme substrate and chromogen if the label is biotin). In addition, the kit may include a container that has a positive control for the probe containing one or more DNA strands with the sequence to be detected and a negative control for the probe that does not contain the DNA strands having any of the sequences to be detected.

Nucleic acid analysis via microarray technology is also applicable to the present invention. In this technique, literally thousands of distinct oligonucleotide probes are built up in an array on a silicon chip. Nucleic acid to be analyzed labeled, e.g., fluorescently, and hybridized to the probes on the chip. It is also possible to study nucleic acid-protein interactions using these nucleic acid microarrays. Using this technique one can determine the presence of mutations or even sequence the nucleic acid being analyzed or one can measure expression levels of a gene of interest. The method is one of parallel processing of many, even thousands, of probes at once and can tremendously increase the rate of analysis.

One method for detecting the amino acid sequences in a protein sample that are associated with LQT syndrome, SQT syndrome, Brugada syndrome and progressive conduction disease as described herein involves the use of an immunoassay employing one or more antibodies that bind to one or more of the mutated amino acid sequences. While the antibodies may be polyclonal or monoclonal, monoclonal antibodies are preferred in view of their specificity and affinity for the antigen.

Polyclonal antibodies may be prepared by well-known methods which involve synthesizing a peptide containing one or more of the amino acid sequences described herein as associated with LQT syndrome, SQT syndrome, Brugada syndrome and progressive conduction disease, purifying the peptide, attaching a carrier protein to the peptide by standard techniques, and injecting a host such as a rabbit, rat, goat, mouse, etc. with the peptide. The sera are extracted from the host by known methods and screened to obtain polyclonal antibodies which are specific to the peptide immunogen. The peptide may be synthesized by the solid phase synthesis method described by Merrifield, R. B., Adv. Enzymol. Relat. Areas Mol. Biol., 32:221-296 (1969) and in "The Chemistry of Polypeptides" (P. G. Katsoyannis, ed.), pp. 336-361, Plenum, N.Y. (1973), the disclosures of which are incorporated herein by reference. The peptide is then purified and may be conjugated to keyhold limpet hemocyanin (KLH) or bovine serum albumin (BSA). This may be accomplished via a sulfhydryl group, if the peptide contains a cysteine residue, using a heterobifunctional crosslinking reagent such as N-maleimido-6-amino caproyl ester of 1-hydroxy-2-nitrobenzene-4-sulfonic acid sodium salt.

The monoclonal antibody will normally be of rodent or human origin because of the availability of murine, rat, and human tumor cell lines that may be used to produce immortal hybrid cell lines that secrete monoclonal antibody. The antibody may be of any isotype, but is preferably an IgG, IgM or IgA, most preferably an IgG2a.

The murine monoclonal antibodies may be produced by immunizing the host with the peptide mentioned above. The host may be inoculated intraperitoneally with an immunogenic amount of the peptide and then boosted with similar amounts of the immunogenic peptide. Spleens or lymphoid tissue is collected from the immunized mice a few days after the final boost and a cell suspension is prepared therefrom for use in the fusion.

Hybridomas may be prepared from the splenocytes or lymphoid tissue and a tumor (myeloma) partner using the general somatic cell hybridization technique of Koehler, B. and Milstein, C., Nature, 256:495-497 (1975) and of Koehler, B. et al., Eur. J. Immunol., 6:511-519 (1976). Suitable myeloma cells for this purpose are those which fuse efficiently, support stable, high-level expression of antibody by the selected antibody-producing cells, and are sensitive to a medium such as HAT medium. Among these, suitable myeloma cell lines are murine myeloma lines, such as those derived from MOPC-21 and MOPC-11 mouse tumors available from the Salk Institute, Cell Distribution Center, San Diego, Calif., USA, or P3X63-Ag8.653 (653) and Sp2/0-Ag14 (SP2/0) myeloma lines available from the American Type Culture Collection, Rockville, Md., USA, under ATCC CRL Nos. 1580 and 1581, respectively.

Basically, the technique may involve fusing the appropriate tumor cells and splenocytes or lymphoid tissue using a fusogen such as polyethylene glycol. After the fusion the cells are separated from the fusion medium and grown on a selective growth medium, such as HAT medium, to eliminate unhybridized parent cells and to select only those hybridomas that are resistant to the medium and immortal. The hybridomas may be expanded, if desired, and supernatants may be assayed by conventional immunoassay procedures (e.g., radioimmunoassay, enzyme immunoassay, or fluorescence immunoassay) using the immunizing agent as antigen. Positive clones may be characterized further to determine whether they meet the criteria of the antibodies of the invention. For example, the antigen-binding ability of the antibodies may be evaluated in vitro by immunoblots, ELISAs and antigen neutralizing tests.

An example of a suitable procedure for making a hybrid cell line that secretes human antibodies against the amino acid genetic markers is somatic cell hybridization using a mouse×human parent hybrid cell line and a human cell line producing sufficiently high levels of such antibodies. The human cell line may be obtained from volunteers immunized with the peptide(s) described above. The human cell line may be transformed with Epstein-Barr virus (EBV) as described, for example, by Foung, et al., J. Immunol. Methods, 70:83-90 (1984).

When EBV transformation is employed, the most successful approaches have been either to pre-select the population of B cells to be transformed or to post-select the antigen-specific transformed populations by panning or rosetting techniques, as described by Kozbar, et al., Scan. J. Immunol., 10:187-194 (1979) and Steinitz, et al., J. Clin. Lab. Immun., 2:1-7 (1979). EBV transformation has been combined with cell fusion to generate human monoclonal antibodies (see, e.g., Foung et al., J. Immun. Meth., 70:83-90 (1984)), due to instability of immunoglobulin secretion by hybridomas when compared to EBV lymphoblastoid cell lines, and higher frequencies of rescue of the antigen-specific populations. EBV most frequently infects and transforms IgM-bearing B cells, but B cells secreting other classes of Ig can also be made into long-term lines using the EBV fusion technique, as described by Brown and Miller, J. Immunol., 128:24-29 (1982).

The cell lines which produce the monoclonal antibodies may be grown in vitro in suitable culture medium such as Iscove's medium, Dulbecco's Modified Eagle's Medium, or RPMI-1640 medium from Gibco, Grand Island, N.Y., or in vivo in syngeneic or immunodeficient laboratory animals. If desired, the antibody may be separated from the culture medium or body fluid, as the case may be, by conventional techniques such as ammonium sulfate precipitation, hydroxyapatite chromatography, ion exchange chromatography, affinity chromatography, electrophoresis, microfiltration, and ultracentrifugation.

The antibodies herein may be used to detect the presence or absence of one or more of the amino acid mutations described herein as associated with LQT syndrome, SQT syndrome, Brugada syndrome and progressive conduction disease. The cells may be incubated in the presence of the antibody, and the presence or absence and/or degree of reaction (antibody-peptide binding) can be determined by any of a variety of methods used to determine or quantitate antibody/antigen interactions (e.g., fluorescence, enzyme-linked immunoassay (ELISA), and cell killing using antibody and complement by standard methods). The antibody employed is preferably a monoclonal antibody.

For use in solid phase immunoassays, the antibodies employed in the present invention can be immobilized on any appropriate solid test support by any appropriate technique. The solid test support can be any suitable insoluble carrier material for the binding of antibodies in immunoassays. Many such materials are known in the art, including, but not limited to, nitrocellulose sheets or filters; agarose, resin, plastic (e.g., PVC or polystyrene) latex, or metal beads; plastic vessels; and the like. Many methods of immobilizing antibodies are also known in the art. See, e.g., Silman et al., Ann. Rev. Biochem., 35:873 (1966); Melrose, Rev. Pure & App. Chem., 21:83 (1971); Cuatrecafas, et al., Meth. Enzym., Vol. 22 (1971). Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. The antibody is attached by simply contacting the protein-coated surface with an aqueous solution of the antibody and allowing it to dry.

Any combination of support and binding technique which leaves the antibody immunoreactive, yet sufficiently immobilizes the antibody so that it can be retained with any bound antigen during a washing, can be employed in the present invention. A preferred solid test support is a plastic bead.

In the sandwich immunoassay, a labeled antibody is employed to measure the amount of antigen bound by the immobilized monoclonal antibody. The label can be any type that allows for the detection of the antibody when bound to a support. Generally, the label directly or indirectly results in a signal which is measurable and related to the amount of label present in the sample. For example, directly measurable labels can include radiolabels (e.g., $^{125}$I, $^{35}$S, $^{14}$C, etc.). A preferred directly measurable label is an enzyme, conjugated to the antibody, which produces a color reaction in the presence of the appropriate substrate (e.g., horseradish peroxidase/o-phenylenediamine). An example of an indirectly measurable label would be antibody that has been biotinylated. The presence of this label is measured by contacting it with a solution containing a labeled avidin complex, whereby the avidin becomes bound to the biotinylated antibody. The label associated with the avidin is then measured. A preferred example of an indirect label is the avidin/biotin system employing an enzyme conjugated to the avidin, the enzyme producing a color reaction as described above. It is to be understood, however, that the term "label" is used in its broadest sense and can include, for example, employing "labeled" antibodies where the label is a xenotypic or isotypic difference from the immobilized antibody, so that the presence of "labeled" antibodies is detectable by incubation with an anti-xenotypic or anti-isotypic antibody carrying a directly detectable label.

Whatever label is selected, it results in a signal which can be measured and is related to the amount of label in a sample. Common signals are radiation levels (when radioisotopes are used), optical density (e.g., when enzyme color reactions are used), and fluorescence (when fluorescent compounds are used). It is preferred to employ a nonradioactive signal, such as optical density (or color intensity) produced by an enzyme reaction. Numerous enzyme/substrate combinations are known in the immunoassay art which can produce a suitable signal. See, e.g., U.S. Pat. Nos. 4,323,647 and 4,190,496, the disclosures of which are incorporated herein.

For diagnostic use, the antibodies may typically be distributed in multicontainer kit form. These kits will typically contain the antibody(ies) in labeled or unlabeled form in suitable containers, any detectable ligand reactive with unlabeled antibody if it is used, reagents for the incubations and washings if necessary, reagents for detecting the label moiety to be detected, such as substrates or derivatizing agents depending on the nature of the label, product inserts and instructions, and a positive control associated with LQT syndrome, SQT syndrome, Brugada syndrome and progressive conduction disease. The antibodies in the kit may be affinity purified if they are polyclonal.

The following examples are included for purposes of illustrating certain aspects of the invention. Accordingly, the examples should not be construed as limiting the subject matter of the present invention.

Example I

KCNH2 Mutations

1. Clinical Evaluation

Family 30-371 (FIG. 1), having 23 members, displayed a high incidence of sudden death. The proband (III-2) was referred due to frequent palpitations. Her ECG displayed a QT interval of 270 msec. Her daughter (IV-5) had a QT interval of 260 msec, but was asymptomatic. The proband's nephew (V-3) had a history of syncope and had a QT interval of 240 msec. The proband's sister (III-1), who had a QT of 210 msec and suffered from atrial fibrillation, died suddenly at age 62; her mother (II-3) died suddenly at age 45 and her nephew died suddenly with documented ventricular fibrillation at age 26 (IV-1). Eight living family members underwent a complete physical examination and a 12-lead ECG as part of their initial clinical work-up. Three presented with a short QT interval and were evaluated with additional tests, including MRI. Two of the affected individuals underwent an electrophysiological study.

Family 30-335, having 16 individuals, included three patients referred for palpitations, syncope and sudden death in one. They also underwent extensive work-up including MRI and two underwent electrophysiological study. Three of the 16 members were affected with short QT syndrome. The proband (IV-2) was referred for history of syncope during exertion and paroxysmal atrial fibrillation. His QT interval ranged from 240 msec to 280 msec. His sister (IV-1) had a long history of palpitations and a QT interval between 220 and 250 msec. Her son (V-1), 6 years old, had suffered aborted sudden death at age 8 months, and had severe neurological damage. His ECG showed a QT interval ranging from 240 to 260 msec. Family history was significant for the death of the probands' brother (IV-3), when he was 3 months old, and their father who died suddenly at age 39 (III-2). Autopsy showed a normal heart in both. There were three other members who died suddenly.

2. Genetic Analysis

Genomic DNA was isolated from peripheral blood leukocytes using a commercial kit (Gentra System, Puregene). Haplotype segregation analysis was performed in family 30-371 by amplification of highly polymorphic markers (Linkage mapping set 2.5 Applied Biosystems) flanking the candidate genes with the use of polymerase chain reaction (PCR). Those genes that were segregating with the affected individuals were further analyzed.

The exons of KCNH2 were amplified and analyzed by direct sequencing using the primers set forth below. PCR products were purified with a commercial reagent (ExoSAP-IT™, USB) and were directly sequenced from both directions with the use of ABI PRISM 3100-Avant™ Automatic DNA Sequencer.

| PRIMERS FOR KCNH2 SCREENING | | Seq. Id. No. |
|---|---|---|
| KCNH2 EXON 1 SENSE | GGCAGACAGGTGTGCCGG | 103 |
| KCNH2 EXON 1 ANTISENSE | CCATCCACACTCGGAAGAG | 104 |
| KCNH2 EXON 2 SENSE | CTGTGTGAGTGGAGAATGTG | 105 |
| KCNH2 EXON 2 ANTISENSE | GTGGTCCCGCCCCTCTTGAC | 106 |
| KCNH2 EXON 3 SENSE | CTTGGGTTCCAGGGTCCATC | 107 |
| KCNH2 EXON 3 ANTISENSE | GACCTTGGACAGCTCACAG | 108 |
| KCNH2 EXON 4 SENSE | GTCCATTTCCCAGGCCTTG | 109 |
| KCNH2 EXON 4 ANTISENSE | GACGTAGTGAAAAGGTCAGAAG | 110 |
| KCNH2 EXON 5 SENSE | GTCTCCACTCTCGATCTATG | 111 |
| KCNH2 EXON 5 ANTISENSE | CCCGGCTCTGGATCACAG | 112 |
| KCNH2 EXON 6 SENSE | CAGAGATGTCATCGCTCCTG | 113 |
| KCNH2 EXON 6 ANTISENSE | CACTACCTCCCACCACATTC | 114 |
| KCNH2 EXON 7 SENSE | CTTGCCCCATCAACGGAATG | 115 |
| KCNH2 EXON 7 ANTISENSE | CTAGCAGCCTCAGTTTCCTC | 116 |
| KCNH2 EXON 8 SENSE | CTGAGACTGAGACACTGAC | 117 |
| KCNH2 EXON 8 ANTISENSE | GTCCTTACTACTGACTGTGAC | 118 |
| KCNH2 EXON 9 SENSE | CTGGAGGTTGAGATTTCTCTG | 119 |
| KCNH2 EXON 9 ANTISENSE | GAAGGCTCGCACCTCTTGAG | 120 |
| KCNH2 EXON 10 SENSE | GTGCCTGCTGCCTGGATG | 121 |
| KCNH2 EXON 10 ANTISENSE | CATTCAATGTCACACAGCAAAG | 122 |
| KCNH2 EXON 11 SENSE | CTGTGTTAAGGAGGGAGCTTG | 123 |
| KCNH2 EXON 11 ANTISENSE | GCCTGGGTAAAGCAGACAC | 124 |
| KCNH2 EXON 12 SENSE | CTCCTCTCTGTTCTCCTCC | 125 |
| KCNH2 EXON 12 ANTISENSE | CAGAGAGCAGAGCTGGGTG | 126 |
| KCNH2 EXON 13 SENSE | CTGTCAGGTATCCCGGGC | 127 |
| KCNH2 EXON 13 ANTISENSE | CAGGACCTGGACCAGACTC | 128 |

-continued

| PRIMERS FOR KCNH2 SCREENING | | Seq. Id. No. |
|---|---|---|
| KCNH2 EXON 14 SENSE | GTGGAGGCTGTCACTGGTG | 129 |
| KCNH2 EXON 14 ANTISENSE | GAAAGGCAGCAAAGCAGGTTTG | 130 |
| KCNH2 EXON 15 A SENSE | GTTCTCCTGCCCCTTTCCC | 131 |
| KCNH2 EXON 15 A ANTISENSE | CTTTCGAGTTCCTCTCCCC | 132 |
| KCNH2 EXON 15 B SENSE | CAGTGTGGACACGTGGCTC | 133 |
| KCNH2 EXON 15 B ANTISENSE | CTATGCATGTCCAGACAGGAAC | 134 |

3. Site-Directed Mutagenesis

C1764A mutation was constructed with the use of GeneTailor™ site-directed mutagenesis system (Invitrogen Corp) with the use of plasmid pcDNA3.1 containing KCNH2 cDNA. The primers for were the following:

```
                                              (Seq. Id. No. 7)
1764F
(5'-GACTCACGCATCGGCTGGCTGCACAAACTGGGCGACCAG-3')
and (Seq. Id. No. 8)
1764R
(5'-GTGCAGCCAGCCGATGCGTGAGTCCATGTGT-3').
```

The mutated plasmid was sequenced to ensure the presence of the C1764A mutation, as well as the absence of other substitutions introduced by the DNA polymerase.

4. In-Vitro Transcription and Mammalian Cell Transfection

KCNH2 and KCNE2 were a kind gift from Drs. A. M Brown (Chantest, Cleveland, Ohio) and S. A. Goldstein (Yale University, New Haven, Conn.), respectively. Both gene constructs were re-cloned from their original vector into pcDNA3.1 (Invitrogen, Carlsbad, Calif.). For transfection, KCNH2 and KCNE2 cDNA were kept at a constant molar ratio of 1:20 to ensure proper expression of both subunits. Modified human embryonic kidney cells (TSA201) were co-transected with the same amounts of pcDNA-KCNH2/KCNE2 and pcDNA-N588K.KCNE2 complex using the calcium phosphate precipitation method. Cells were grown on polylysine coated 35 mm culture dishes and placed in a temperature-controlled chamber for electrophysiological study (Medical Systems, Greenvale N.Y.) 2 days post-transfection.

5. Electrophysiology

Standard whole cell patch clamp technique was used to measure currents in transfected TSA201 cells. All recordings were made at room temperature using an Axopatch 1D amplifier equipped with a CV-4 1/100 headstage (Axon Instruments). Cells were superfused with HEPES-buffered solution containing (in mmol/L): 130 NaCl, 5 KCl, 1.8 $CaCl_2$, 1. $MgCl_2$, 2.8 Na acetate, 10 Hepes, pH 7.3 with NaOH/HCl. Patch pipettes were pulled from borosilicate (7740) or flint glass (1161) (PP89 Narahige Japan) to have resistances between 2 and 4 MΩ when filled with a solution containing (in mmol/L): 20 KCl, 120 KF, 1.0 $MgCl_2$, 10 HEPES and EGTA, pH 7.2 (KOH/HCl). Currents were filtered with a four pole Bessel filter at 0.5 to 1 kHz, digitized at 1 kHz and stored on the hard disk of an IBM compatible computer. All data acquisition and analysis was performed using the suite of pCLAMP programs V7 or V6 (Axon Instruments, CA).

Example II

SCN5A and KCNQ1 Mutations

1. Genetic Analysis

Genomic DNA was isolated from peripheral blood leukocytes using a commercial kit (Gentra System, Puregene). Haplotype segregation analysis was performed in family 30-371 by amplification of highly polymorphic markers (Linkage mapping set 2.5 Applied Biosystems) flanking the candidate genes with the use of polymerase chain reaction (PCR). Those genes that were segregating with the affected individuals were further analyzed.

The exons of SCN5A and KCNQ1 were amplified and analyzed by direct sequencing using the primers set forth below. PCR products were purified with a commercial reagent (ExoSAP-IT™, USB) and were directly sequenced from both directions with the use of ABI PRISM 3100-Avant™ Automatic DNA Sequencer.

| PRIMERS FOR SCN5A SCREENING | | Seq. Id. No. |
|---|---|---|
| SCN5A EXON 2 SENSE | GGTCTGCCCACCCTGCTCTCT | 9 |
| SCN5A EXON 2 ANTISENSE | CCTCTTCCCCCTCTGCTCCATT | 10 |
| SCN5A EXON 3 SENSE | AGTCCAAGGGCTCTGAGCAA | 11 |
| SCN5A EXON 3 ANTISENSE | GGTACTCAGCAGGTATTAACTGCAA | 12 |
| SCN5A EXON 4 SENSE | GGTAGCACTGTCCTGGCAGTGAT | 13 |
| SCN5A EXON 4 ANTISENSE | CCTGGACTCAAGTCCCCTTC | 14 |
| SCN5A EXON 5 SENSE | TCACTCCACGTAAGGAACCTG | 15 |
| SCN5A EXON 5 ANTISENSE | ATGTGGACTGCAGGGAGGAAGC | 16 |
| SCN5A EXON 6 SENSE | CCTTTCCTCCTCTCACTGTCTGT | 17 |
| SCN5A EXON 6 ANTISENSE | GGTATTCTGGTGACAGGCACATTC | 18 |
| SCN5A EXON 7 SENSE | CCACCTCTGGTTGCCTACACTG | 19 |
| SCN5A EXON 7 ANTISENSE | GTCTGCGGTCTCACAAAGTCTTC | 20 |
| SCN5A EXON 8 SENSE | CGAGTGCCCCTCACCAGCATG | 21 |
| SCN5A EXON 8 ANTISENSE | GGAGACTCCCCTGGCAGGACAA | 22 |
| SCN5A EXON 9 SENSE | GGGAGACAAGTCCAGCCCAGCAA | 23 |
| SCN5A EXON 9 ANTISENSE | AGCCCACACTTGCTGTCCCTTG | 24 |
| SCN5A EXON 10 SENSE | ACTTGGAAATGCCCTCACCCAGA | 25 |

-continued

| | | Seq. Id. No. |
|---|---|---|
| SCN5A EXON 10 ANTISENSE | CACCTATAGGCACCATCAGTCAG | 26 |
| SCN5A EXON 11 SENSE | AAACGTCCGTTCCTCCACTCT | 27 |
| SCN5A EXON 11 ANTISENSE | AACCCACAGCTGGGATTACCATT | 28 |
| SCN5A EXON 12A SENSE | GCCAGTGGCTCAAAAGACAGGCT | 29 |
| SCN5A EXON 12A ANTISENSE | CCTGGGCACTGGTCCGGCGCA | 30 |
| SCN5A EXON 12B SENSE | CACCACACATCACTGCTGGTGC | 31 |
| SCN5A EXON 12B ANTISENSE | GGAACTGCTGATCAGTTTGGGAGA | 32 |
| SCN5A EXON 13 SENSE | CCCTTTTCCCCAGCTGACGCAAA | 33 |
| SCN5A EXON 13 ANTISENSE | GTCTAAAGCAGGCCAAGACAAATG | 34 |
| SCN5A EXON 14 SENSE | CAGGAAGGTATTCCAGTTACATATGA | 35 |
| SCN5A EXON 14 ANTISENSE | ACCCATGAAGCTGTGCCAGCTGT | 36 |
| SCN5A EXON 15 SENSE | CTTTCCTATCCCAAACAATACCT | 37 |
| SCN5A EXON 15 ANTISENSE | CCCCACCATCCCCCATGCAGT | 38 |
| SCN5A EXON 16 SENSE | GAGCCAGAGACCTTCACAAGGTC-CCCT | 39 |
| SCN5A EXON 16 ANTISENSE | CCCTTGCCACTTACCACAAG | 40 |
| SCN5A EXON 17A SENSE | GGGACTGGATGGCTTGGCATGGT | 41 |
| SCN5A EXON 17A ANTISENSE | CGGGGAGTAGGGGGTGGCAATG | 42 |
| SCN5A EXON 17B SENSE | GCCCAGGGCCAGCTGCCCAGCT | 43 |
| SCN5A EXON 17B ANTISENSE | CTGTATATGTAGGTGCCTTATACATG | 44 |
| SCN5A EXON 18 SENSE | AGGGTCTAAACCCCCAGGGTCA | 45 |
| SCN5A EXON 18 ANTISENSE | CCCAGCTGGCTTCAGGGACAAA | 46 |
| SCN5A EXON 19 SENSE | GAGGCCAAAGGCTGCTACTCAG | 47 |
| SCN5A EXON 19 ANTISENSE | CCTGTCCCCTCTGGGTGGAACT | 48 |
| SCN5A EXON 20 SENSE | ACAGGCCCTGAGGTGGGCCTGA | 49 |
| SCN5A EXON 20 ANTISENSE | TGACCTGACTTTCCAGCTGGAGA | 50 |
| SCN5A EXON 21 SENSE | TCCAGGCTTCATGTCCACCTGTCT | 51 |
| SCN5A EXON 21 ANTISENSE | TCTCCCGCACCGGCAATGGGT | 52 |
| SCN5A EXON 22 SENSE | AGTGGGGAGCTGTTCCCATCCT | 53 |
| SCN5A EXON 22 ANTISENSE | GGACCGCCTCCCACTCC | 54 |
| SCN5A EXON 23 SENSE | TTGAAAAGGAAATGTGCTCTGGG | 55 |
| SCN5A EXON 23 ANTISENSE | AACATCATGGGTGATGGCCAT | 56 |
| SCN5A EXON 24 SENSE | CTCAAGCGAGGTACAGAATTAAATGA | 57 |
| SCN5A EXON 24 ANTISENSE | GGGCTTTCAGATGCAGACACTGAT | 58 |
| SCN5A EXON 25 SENSE | GCCTGTCTGATCTCCCTGTGTGA | 59 |
| SCN5A EXON 25 ANTISENSE | CCTGTCTGGTCTCCCTGTGTCA | 60 |
| SCN5A EXON 26 SENSE | CCATGCTGGGGCCTCTGAGAAC | 61 |
| SCN5A EXON 26 ANTISENSE | GGCTCTGATGGCTGGCCATGTG | 62 |
| SCN5A EXON 27 SENSE | CCCAGCGAGCACTTTCCATTTG | 63 |
| SCN5A EXON 27 ANTISENSE | GCTTCTCCGTCCAGCTGACTTGTA | 64 |
| SCN5A EXON 28A SENSE | TGCACAGTGATGCTGGCTGGAA | 65 |
| SCN5A EXON 28A ANTISENSE | GAAGAGGCACAGCATGCTGTTGG | 66 |
| SCN5A EXON 28B SENSE | AAGTGGGAGGCTGGCATCGAC | 67 |
| SCN5A EXON 28B ANTISENSE | GTCCCCACTCACCATGGGCAG | 68 |
| SCN5A EXON 28C SENSE | GTCCTGTCTGACTTTGCCGAC | 69 |
| SCN5A EXON 28C ANTISENSE | CATTTCTTACTCCCAAAGCCAG | 70 |
| PRIMERS FOR KCNQ1 SCREENING | | |
| KCNQ1 EXON 1 SENSE | CTTGAGTGTGGAGGAGATAAGC | 71 |
| KCNQ1 EXON 1 ANTISENSE | CAAATTCCCGAGAGCCAGAAAC | 72 |
| KCNQ1 EXON 2 SENSE | CAGGTGCATCTGTGGGATG | 73 |

-continued

| | | Seq. Id. No. |
|---|---|---|
| KCNQ1 EXON 2 ANTISENSE | GGACCAATGTGTGGGCAAG | 74 |
| KCNQ1 EXON 3 SENSE | GTTCAAACAGGTTGCAGGGTC | 75 |
| KCNQ1 EXON 3 ANTISENSE | CTTAGGGGACTCCATCTGGTAG | 76 |
| KONQ1 EXON 4 SENSE | GTGTATGCTCTTCCCTGGG | 77 |
| KCNQ1 EXON 4 ANTISENSE | GCATCTGAGCAAGGTGGATG | 78 |
| KCNQ1 EXON 5 SENSE | CGTGAACAGCTGAGCCCAG | 79 |
| KCNQ1 EXON 5 ANTISENSE | CATCTCAAGCTGTCCTAGTGTG | 80 |
| KCNQ1 EXON 6 SENSE | GACTCGCTGCCTTAGGCG | 81 |
| KCNQ1 EXON 6 ANTISENSE | GAAGTCTCAAGACACCAGTG | 82 |
| KCNQ1 EXON 7 SENSE | CATCAGAGTGGTGGGTTTG | 83 |
| KCNQ1 EXON 7 ANTISENSE | CTGAACGTAAGTGGGTCTG | 84 |
| KCNQ1 EXON 8 SENSE | CAACGGTGACCGGTAACCAC | 85 |
| KCNQ1 EXON 8 ANTISENSE | CTGGATGCAACAATAACAGTGAC | 86 |
| KCNQ1 EXON 9 SENSE | GAGCTGTAGCTTCCATAAGG | 87 |
| KCNQ1 EXON 9 ANTISENSE | CTGTACCAAGCCAAATGCATG | 88 |
| KCNQ1 EXON 10 SENSE | CTGTCCGGGTGTATGTGGC | 89 |
| KCNQ1 EXON 10 ANTISENSE | CAAAAAGGCAGTGACCTTC | 90 |
| KCNQ1 EXON 11 SENSE | CACAGCACTGGCAGGTTG | 91 |
| KCNQ1 EXON 11 ANTISENSE | GGCCAGAGAGCAAGGCTTC | 92 |
| KCNQ1 EXON 12 SENSE | CAGTCTGCGTGCTCCTCAG | 93 |
| KCNQ1 EXON 12 ANTISENSE | CCTTGACACCCTCCACTATG | 94 |
| KCNQ1 EXON 13 SENSE | CAGGTCTTCACAAGCCTCC | 95 |
| KONQ1 EXON 13 ANTISENSE | GTTGAGAGGCAAGAACTCAG | 96 |
| KCNQ1 EXON 14 SENSE | CAAGCTGTCTGTCCCACAG | 97 |
| KCNQ1 EXON 14 ANTISENSE | CTGGCTTTCATTTCATGTCATG | 98 |
| KCNQ1 EXON 15 SENSE | GTAGGTTTAGGCATTTTGACTC | 99 |
| KCNQ1 EXON 15 ANTISENSE | CTTCACGTTCACACGCAGAC | 100 |
| KCNQ1 EXON 16 SENSE | CTGAGGCTGTCTGCACAC | 101 |
| KCNQ1 EXON 16 ANTISENSE | GTGGCCTCCTTCAGAGAG | 102 |

2. In Vitro Transcription and Mammalian Cell Transfection

Gene constructs were re-cloned from their original vector into pcDNA3.1 (Invitrogen Carlsbad, Calif.). F532C mutation was constructed with the GeneTailor™ site-directed mutagenesis system (Invitrogen Corp) on plasmid pcDNA3.1 containing the appropriate primers. The mutated plasmid was sequenced to ensure the presence of mutation without spurious substitutions. Modified human embryonic kidney cells (TSA201) were co-transected with the same amounts of pcDNA using the calcium phosphate precipitation method. Cells were grown on polylysine coated 35 mm culture dishes and placed in a temperature-controlled chamber for electrophysiological study (Medical Systems, Greenvale N.Y.) 2 days post-transfection.

3. Electrophysiology

Voltage clamp recordings were made using patch pipettes fabricated from borosilicate glass capillaries (1.5 mm O.D., Fisher Scientific, Pittsburg, Pa.). The pipettes were pulled using a gravity puller (Narashige Corp.) and filled with pipette solution of the following composition (mM): 10 KCl, 105 CsF, 10 NaCl, 10 HEPES, 10 EGTA and 5 TEACl, pH=7.2 with CsOH. The pipette resistance ranged from 0.8-2.8 MΩ when filled with the internal solution. The perfusion solution contained (mM): 130 NaCl, 5 KCl, 1.8 $CaCl_2$, 1.0 $MgCl_2$, 2.8 Na acetate, 10 HEPES, 10 glucose, pH=7.3 with NaOH. Current signals were recorded using a MultiClamp 700A amplifier (Axon Instruments Inc., Foster City, Calif.) and series resistance errors were reduced by about 60-70% with electronic compensation. All signals were acquired at 20-50 kHz (Digidata 1322, Axon Instruments) and analyzed with a microcomputer running pClamp 9 software (Axon Instruments, Foster City, Calif.). All recordings were made at room temperature.

Example III

Correlation of Gene Mutation to Syndrome

Using the techniques described above, the following mutations were shown to correspond with the indicated clinical conditions:

| Patient | FAMILY | Channel | Exon | Aminoacid position |
|---|---|---|---|---|
| BRUGADA SYNDROME | | | | |
| RB4901 | 24-310 | SCN5A | 28 | C1727R |
| RB5145 | 24-345 | SCN5A | 3 | R104W |
| RB5037 | 24-328 | SCN5A | 16 | insertionTG (851) |
| RB4665 | 24-064 | SCN5A | 16 | R878C |
| RB5151 | 24-JPN3 | SCN5A | 12 | F532C |
| RB6011 | 24-365 | SCN5A | 16 | L917R |
| RB6130 | 33-433 | SCN5A | 6, 22 | V232I + L1307F |
| RB054 | 24-011 | SCN5A | 27splice28 | deletion(E1573-G1604) |
| RB5029 | 24-284 | SCN5A | 14 | A735V |
| RB6237 | 24-483 | SCN5A | 27 | E1573K |
| RB6026 | 24-372 | SCN5A | 5 | R179 stop |
| RB6179 | 25-440 | SCN5A | 10 | E446K |
| RB6181 | 25-442 | SCN5A | 10 | G400A |
| RB6267 | 24-492 | SCN5A | 16 | H886P |
| RB6042 | 24-347 | SCN5A | 9, 28 | P336L, I1659V |
| RB4060 | 24-096 | SCN5A | 28 | Y1614 stop codon |
| RB4510 | | SCN5A | 6 | T220I |
| LONG QT SYNDROME | | | | |
| RB6024 | 25-JPN1 | KCNQ1 | 3 | G189W |
| RB6301 | 25-499 | KCNH2 | 5 | R356H |
| RB6087 | 25-387 | SCN5A | 19 | S1134l |
| RB6188 | 25-449 | KCNH2 | 9 | C deletion (764) |
| RB6194 | 25-454 | KCNH2 | 6 | W398stopcodon |
| SHORT QT SYNDROME | | | | |
| RB6019 | 30-371 | KCNH2 | 7 | N588K |
| PROGRESSIVE CONDUCTION DISEASE | | | | |
| RB6325 | 25-510 | SCN5A | 17 | P1008S |

It will be understood that various modifications may be made to the embodiments and examples disclosed herein. Therefore, the above description should not be construed as limiting, merely as exemplifications of preferred embodiments. Those skilled in the art may envision other modifications within the spirit and scope of the claims appended hereto.

What is claimed is:

1. An isolated nucleic acid encoding a mutant SCN5A protein corresponding to wild-type human SCN5A protein (SEQ ID NO: 3), the mutant SCN5A protein differs from SEQ ID NO:3 by having a mutation selected from the group consisting of R104W, R179 stop, G400A, E446K, F532C, R878C, P1008S, E1573K, and P336L+I1659V.

2. An isolated vector comprising the isolated nucleic acid of claim 1.

3. An isolated cell comprising the isolated nucleic acid of claim 1.

* * * * *